US011331442B2

(12) United States Patent
Ferriter et al.

(10) Patent No.: US 11,331,442 B2
(45) Date of Patent: May 17, 2022

(54) DRUG DELIVERY SYSTEMS AND RELATED METHODS

(71) Applicant: Pearl Therapeutics, Inc., Redwood City, CA (US)

(72) Inventors: Matthew Ferriter, Chapel Hill, NC (US); Denny Himel, Cary, NC (US); Brian Foster, Apex, NC (US); Michael L. King, Durham, NC (US); Dan Deaton, New Hill, NC (US); Fred Hamlin, Cambridge (GB); Jill Sherwood, Raleigh, NC (US); Sarvajna Kumar Dwivedi, Redwood City, CA (US); Robert V. Sheehy, Jr., N. Attleboro, MA (US)

(73) Assignee: Pearl Therapeutics, Inc., Redwood City, CA (US)

( * ) Notice: Subject to any disclaimer, the term of this patent is extended or adjusted under 35 U.S.C. 154(b) by 0 days.

(21) Appl. No.: 17/487,997

(22) Filed: Sep. 28, 2021

(65) Prior Publication Data

US 2022/0016366 A1    Jan. 20, 2022

Related U.S. Application Data

(63) Continuation of application No. 16/754,585, filed as application No. PCT/US2018/054721 on Oct. 5, 2018.

(Continued)

(51) Int. Cl.
    *A61M 15/00*    (2006.01)
(52) U.S. Cl.
    CPC ...... *A61M 15/009* (2013.01); *A61M 15/0026* (2014.02); *A61M 15/0068* (2014.02); *A61M 2202/062* (2013.01)

(58) Field of Classification Search
    CPC ............ A61M 15/009; A61M 15/0026; A61M 15/0068; A61M 2202/062; A61M 11/00;
    (Continued)

(56) References Cited

U.S. PATENT DOCUMENTS

| 3,826,413 A | 7/1974 | Warren |
| 4,576,157 A | 3/1986 | Raghuprasad |

(Continued)

FOREIGN PATENT DOCUMENTS

| CN | 106620970 A | 5/2017 |
| GB | 2 451 833 A | 2/2009 |

(Continued)

OTHER PUBLICATIONS

International Search Report and Written Opinion of the International Searching Authority for international application No. PCT/US2018/054721, dated Jan. 28, 2019, 16 pages.

*Primary Examiner* — Victoria Murphy
(74) *Attorney, Agent, or Firm* — Seed IP Law Group LLP

(57) ABSTRACT

Systems and methods for isolating and/or desiccating a portion of a drug delivery tract of a drug delivery apparatus to reduce water vapor content therein are provided. For example, there is provided a metered dose inhaler for delivering aerosolized medicament or other matter to a user. The aerosolized medicament or other matter may be discharged from a discharge passageway within the inhaler into an inhalation passageway for inhalation by a user, and the inhaler may comprise a seal member operative to selectively isolate the discharge passageway from the inhalation passageway and external environment during inactivity. The inhaler may further comprise a desiccant material arranged to withdraw moisture from the isolated discharge passageway. In other instances, desiccant material may be arranged to withdraw moisture from the discharge passageway of the (Continued)

inhaler without isolating the discharge passage during inactivity.

15 Claims, 19 Drawing Sheets

Related U.S. Application Data

(60) Provisional application No. 62/639,911, filed on Mar. 7, 2018, provisional application No. 62/569,901, filed on Oct. 9, 2017.

(58) Field of Classification Search
CPC .. A61M 11/06; A61M 11/08; A61M 15/0091; B05B 11/3053; B65D 83/386
See application file for complete search history.

(56) References Cited

U.S. PATENT DOCUMENTS

| | | |
|---|---|---|
| 5,184,761 A | 2/1993 | Lee |
| 5,263,475 A | 11/1993 | Altermatt et al. |
| 5,297,542 A | 3/1994 | Bacon |
| 5,349,944 A | 9/1994 | Chippendale et al. |
| 6,197,280 B1 | 3/2001 | Goodman et al. |
| 6,354,290 B1 | 3/2002 | Howlett |
| 6,460,537 B1 | 10/2002 | Bryant et al. |
| 6,886,560 B1 | 5/2005 | Seppälä |
| 2002/0144678 A1 | 10/2002 | Warby |
| 2003/0051727 A1* | 3/2003 | Haan ............... A61M 15/009 128/200.11 |
| 2003/0180228 A1* | 9/2003 | Cripps ............... B65D 77/003 128/200.23 |
| 2004/0089293 A1 | 5/2004 | Johnson et al. |
| 2006/0225732 A1 | 10/2006 | Djupesland |
| 2007/0125371 A1 | 6/2007 | Djupesland |
| 2008/0173301 A1 | 7/2008 | Deaton et al. |
| 2009/0050149 A1 | 2/2009 | Von Schuckmann |
| 2012/0180785 A1 | 7/2012 | Trill et al. |

FOREIGN PATENT DOCUMENTS

| | | | |
|---|---|---|---|
| JP | 2927479 B2 | 7/1999 | |
| JP | 2004-510558 A | 4/2004 | |
| WO | 90/02576 A1 | 3/1990 | |
| WO | 02/30499 A2 | 4/2002 | |
| WO | 2007/022573 A1 | 3/2007 | |
| WO | WO-2009029029 A1 * | 3/2009 | ........ A61M 15/0015 |

* cited by examiner

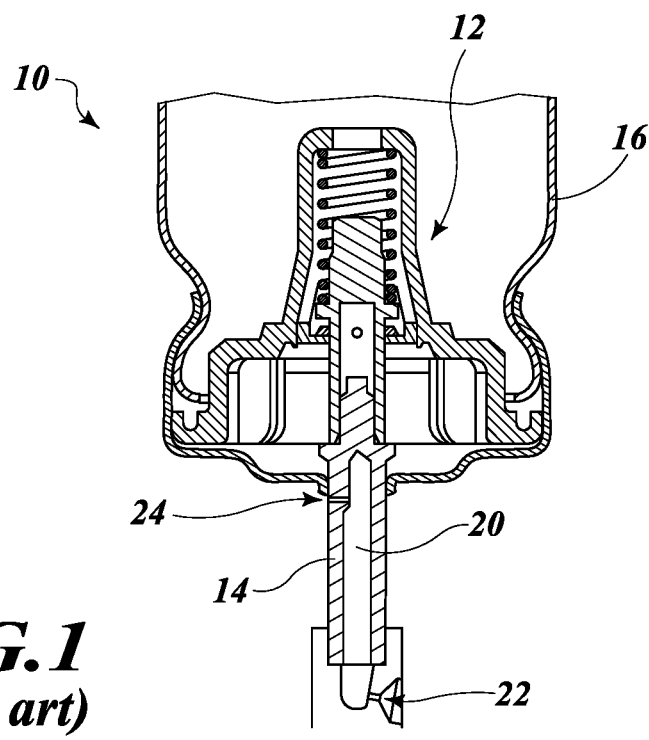
FIG.1
*(prior art)*
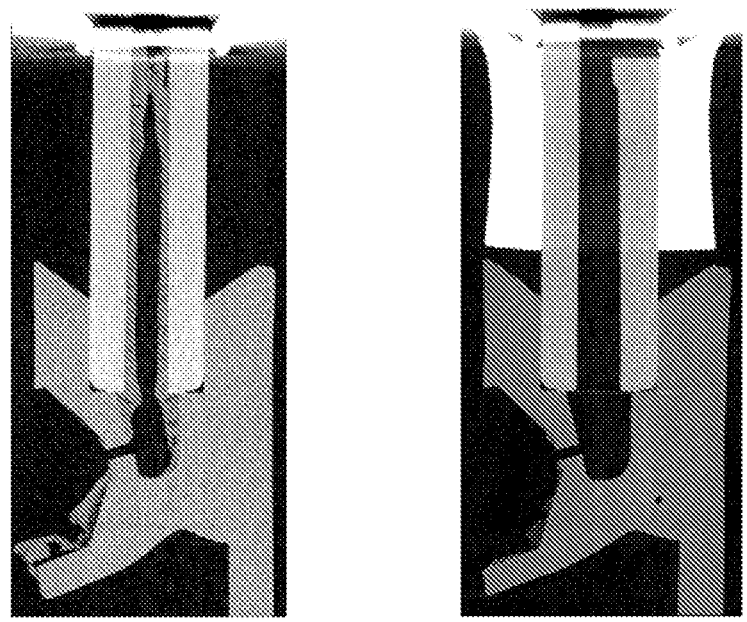
FIG.2A
*(prior art)*
FIG.2B

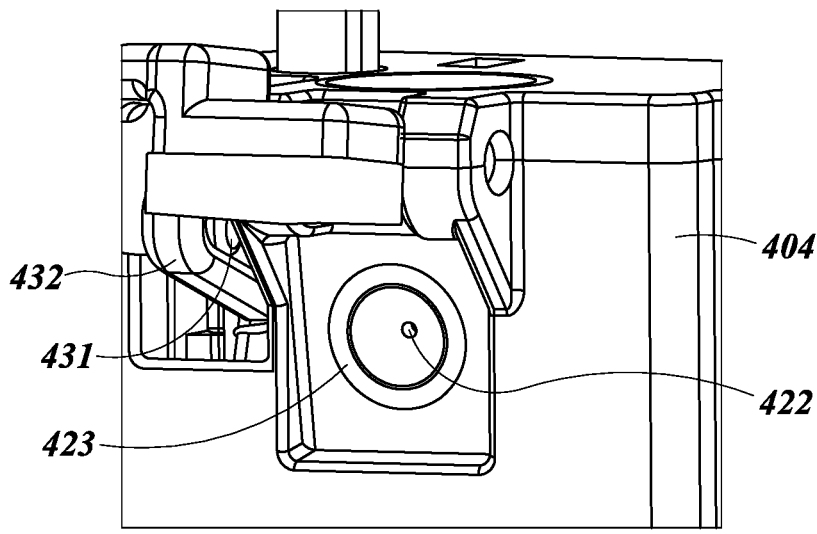
FIG.8
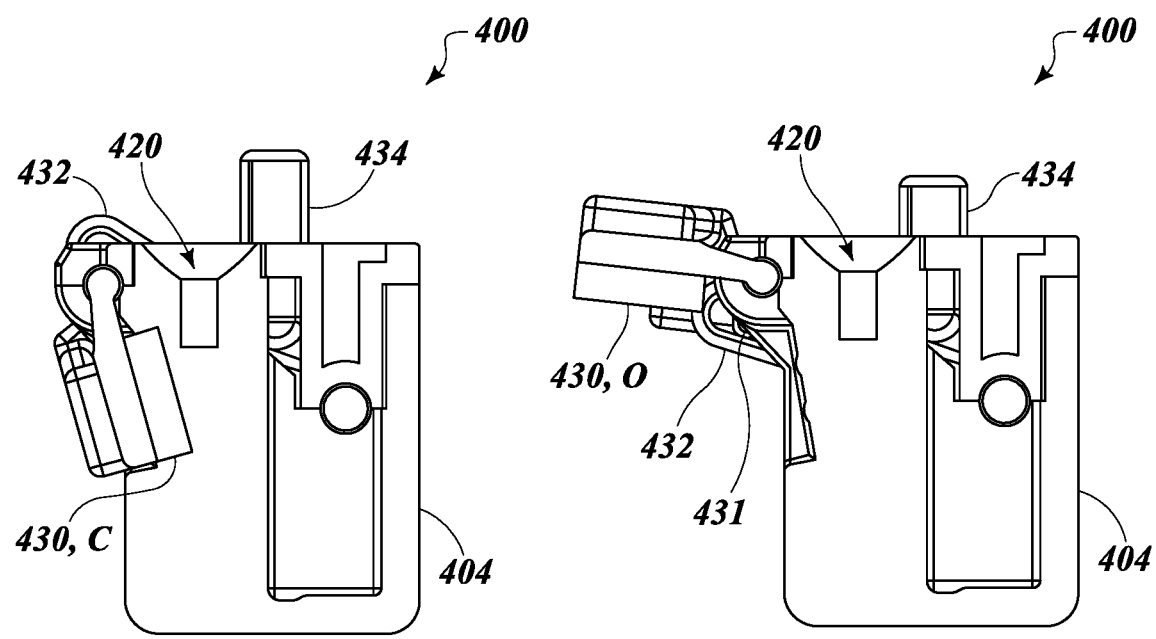
FIG.9A  FIG.9B

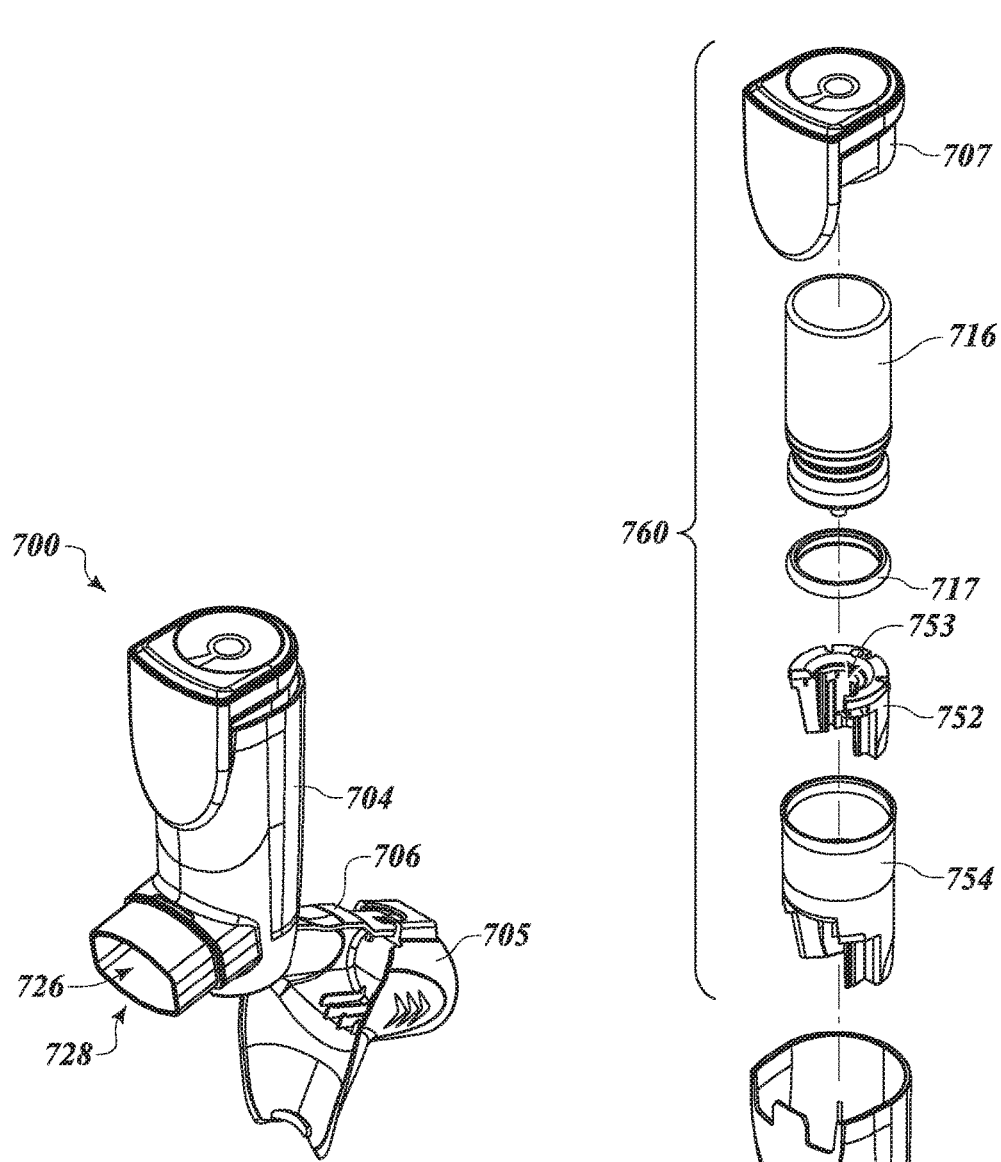
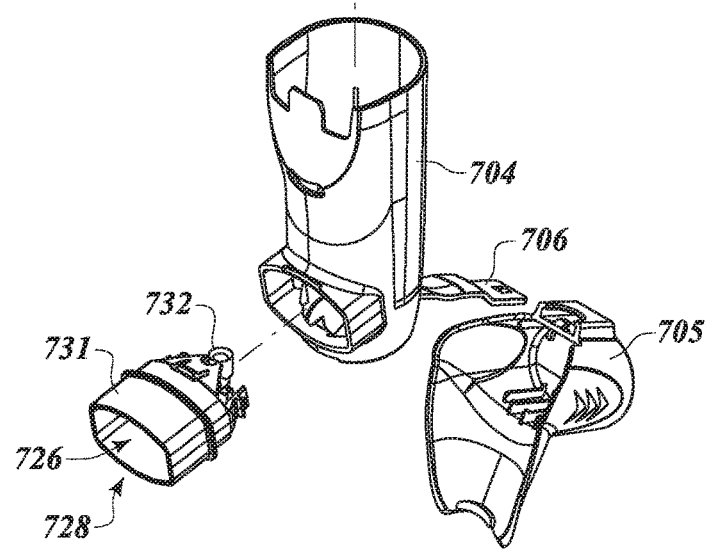
FIG.19
FIG.20

DRUG DELIVERY SYSTEMS AND RELATED METHODS

CROSS-REFERENCE TO RELATED APPLICATIONS

This application is a continuation of U.S. patent application Ser. No. 16/754,585, filed Apr. 8, 2020, which is a national stage of international application No. PCT/US2018/054721, filed Oct. 5, 2018, which claims the benefit of U.S. Provisional Patent Application No. 62/569,901, filed Oct. 9, 2017, and U.S. Provisional Patent Application No. 62/639,911, filed Mar. 7, 2018, the contents of which are hereby incorporated by reference in their entirety.

BACKGROUND

Technical Field

This disclosure generally relates to drug delivery systems and related methods, and, more particularly, to drug delivery systems and methods for isolating and/or desiccating a portion of a drug delivery tract of a drug delivery apparatus to reduce water vapor content therein. Examples include aerosol delivery units suitable for delivering a dose of aerosolized matter for inhalation by a user while preventing or minimizing the deposition of matter (e.g., buildup of hygroscopic drug product) within a discharge passageway thereof, or from other detrimental effects arising from moisture infiltration into the aerosol delivery unit.

Description of the Related Art

It is well known to treat patients with medicaments contained in an aerosol, for example, in the treatment of respiratory disorders. It is also known to use for such treatment, medicaments which are contained in an aerosol and are administered to a patient by means of an inhalation device comprising a mouthpiece and a housing in which an aerosol canister is loaded. Such inhalation devices are generally referred to as metered dose inhalers (MDIs). The aerosol canisters used in such inhalation devices are designed to deliver a predetermined dose of medicament upon each actuation by means of an outlet valve member (e.g., metering slide valve) at one end which can be opened either by depressing the valve member while the canister is held stationary or by depressing the canister while the valve member is held stationary. In the use of such devices, the aerosol canister is placed in the housing with the outlet valve member of the canister communicating with the mouthpiece. When used for dispensing medicaments, for example, in bronchodilation therapy, the patient holds the housing in a more or less upright position and the mouthpiece of the inhalation device is placed in the mouth of the patient. The aerosol canister is then actuated to dispense a dose of medicament from the canister which is then inhaled by the patient. The effective delivery of medicament to the patient using an inhalation device such as a conventional MDI may be hindered by the deposition and accumulation of the discharged medicament or other matter within the discharge passageway (e.g., buildup of hygroscopic drug product in the valve stem), or from other detrimental effects arising from moisture infiltration into the device. The same or similar effects may arise in the drug delivery tract of other drug delivery apparatuses, such as, for example, dry powder inhalers (DPIs) and drug injectors.

BRIEF SUMMARY

Embodiments described herein provide systems and methods for isolating and/or desiccating a portion of a drug delivery tract of a drug delivery apparatus to reduce water vapor content therein. This includes, for example, aerosol delivery systems and related methods particularly well suited for delivering a dose of aerosolized matter in an efficient and reliable manner for inhalation by a user while preventing or minimizing the deposition of matter within a discharge passageway thereof, or otherwise minimizing or eliminating other detrimental effects that may arise from moisture infiltration into the system. Embodiments include, for example, aerosol delivery systems featuring devices and techniques for selectively sealing at least a portion of the discharge passageway when the aerosol delivery system is not being used to discharge the medicament and/or for exposing the discharge passageway to a desiccant material to remove moisture therefrom. It has been found that sealing the discharge passageway and removing moisture therefrom can, in connection with at least some products, substantially eliminate or significantly reduce the deposition or accumulation of matter within the discharge passageway which may otherwise hinder consistent delivery (e.g., consistent shot weight) of the discharged medicament or other aerosolized matter. Embodiments of the aerosol delivery systems with onboard desiccant material may advantageously eliminate the need for traditional desiccant materials that are often provided within product packaging for moisture control purposes. In addition, in some instances, embodiments may sufficiently minimize detrimental effects associated with moisture exposure and eliminate the need for foil overwrap or other techniques used to enhance product shelf life. Still further, benefits of the moisture management techniques disclosed herein may extend moisture protection beyond initial product storage to provide moisture control functionality throughout usable product life.

In addition, inhaler embodiments disclosed herein featuring devices and techniques for selectively sealing at least a portion of the discharge passageway may enable unsealing and sealing of the discharge passageway with minimal impact on the actuation force or canister return force. Moreover, inhaler embodiments may allow for unsealing and sealing of the discharge passageway in timed coordination with the discharge of aerosolized matter so as to not impact or hinder the flow path of such matter. In this way, benefits of the embodiments disclosed herein may be realized without appreciably or unduly hindering the operation and effectiveness of the aerosol delivery systems. Disclosed embodiments may also operate similar to inhaler devices lacking such features or functionality for selectively sealing the discharge passageway and/or exposing the same to a desiccant material such that users may be unaware of the additional features and functionality during use.

The drug delivery systems described herein, in certain embodiments, are suited to delivery of aerosol formulations that include one or moisture sensitive components or exhibit a high solids content. For example, moisture sensitive components include any material that, when exposed to ambient moisture or condensation events such as those associated with aerosolization of a medicament delivered from a metered dose inhaler, may absorb or adsorb water in a manner that leads to increased deposition of the material within the discharge passageway of an aerosol delivery system.

BRIEF DESCRIPTION OF THE SEVERAL VIEWS OF THE DRAWINGS

FIG. 1 is a cross-sectional view of a conventional canister of an MDI showing an outlet valve member thereof, which includes a movable valve stem extending from a canister body thereof, the valve stem defining a portion of a discharge passageway extending from the canister body to a discharge orifice provided within the MDI.

FIG. 2A is a CT scan of a discharge passageway of a conventional MDI, showing the deposition or accumulation of matter therein arising from repeated use of the device.

FIG. 2B is a CT scan of a discharge passageway of an MDI according to certain aspects and techniques of the present invention, showing the discharge passageway substantially free of deposited or accumulated matter despite repeated use of the MDI to dispense medicament.

FIG. 8 is a skewed isometric view of a portion of an aerosol delivery unit, according to yet another example embodiment, in which a seal member thereof is in an open position.

FIG. 9A is a cross-sectional side view of the portion of the aerosol delivery unit of FIG. 8 with the seal member in a closed position.

FIG. 9B is a cross-sectional side view of the portion of the aerosol delivery unit of FIG. 8 with the seal member in the open position.

FIG. 19 is an isometric view of an aerosol delivery unit, according to yet another example embodiment.

FIG. 20 is an exploded isometric view of the aerosol delivery unit of FIG. 19.

DETAILED DESCRIPTION

In the following description, certain specific details are set forth in order to provide a thorough understanding of various disclosed embodiments. However, one of ordinary skill in the relevant art will recognize that embodiments may be practiced without one or more of these specific details. In other instances, well-known structures and devices associated with MDIs or other drug delivery devices or components may not be shown or described in detail to avoid unnecessarily obscuring descriptions of the embodiments.

Figure 3:
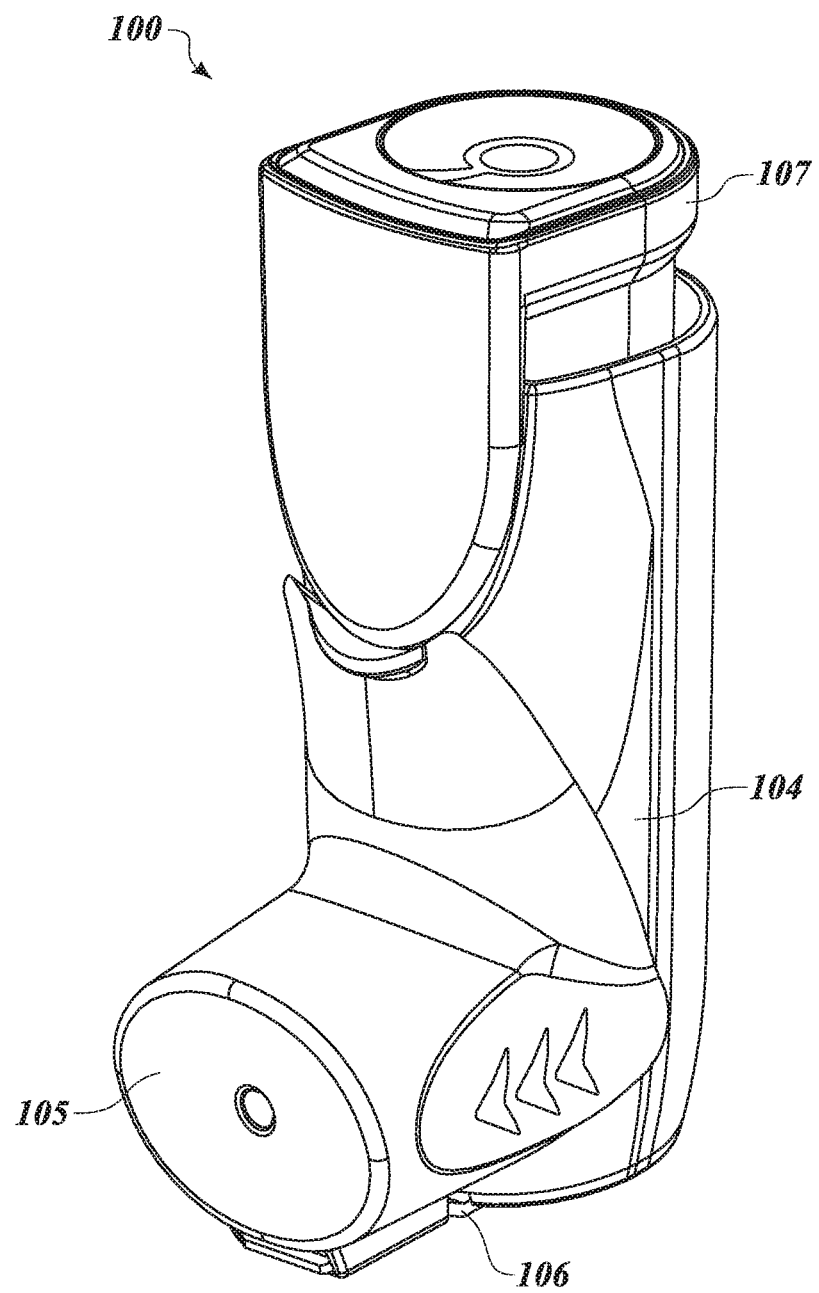
FIG. 3 is an isometric view of an aerosol delivery unit, according to one example embodiment.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Embodiments described herein provide systems and methods for isolating and/or desiccating a portion of a drug delivery tract of a drug delivery apparatus to reduce water vapor content therein. This includes, for example, aerosol delivery systems and related methods particularly well suited for delivering a dose of aerosolized matter in an efficient and reliable manner for inhalation by a user while preventing or minimizing the deposition of matter within a discharge passageway of the delivery unit throughout repeated use thereof. Embodiments include, for example, aerosol delivery systems comprising a seal member to selectively seal off at least a portion of a discharge passageway of the device when not actively discharging aerosolized matter therethrough. Embodiments of the delivery systems may further include a desiccant material in fluid communication with the discharge passageway to assist in withdrawing moisture therefrom. Advantageously, the systems and methods described herein may assist in ensuring consistent delivery of the aerosolized matter (e.g., consistent shot weight) which may otherwise be compromised by fouling of the discharge passageway. Other advantages will be appreciated from a detailed review of the present disclosure.

Although the drug delivery systems described herein are shown and described largely in the context of metered dose inhalers (MDIs) for delivering medicament or other aerosolized matter to a user, it will be appreciated by those of ordinary skill in the relevant art that features and aspects of such systems may applied to other devices and for other purposes, including other drug delivery apparatuses having one or more drug delivery tracts.

By way of background, FIG. 1 shows a cross-sectional view of a conventional canister 10 of an MDI showing an outlet valve member 12 thereof, which includes a movable valve stem 14 extending from a canister body 16 that contains the matter to be discharged. The valve stem 14 defines a portion of a discharge passageway 20 extending from the canister body 16 to a discharge orifice 22 provided within the MDI. As will be appreciated by those of ordinary skill in the relevant art, when the valve stem 14 is displaced relative to the canister body 16, a metered dose of the matter contained with the canister body 16 is discharged through the discharge orifice 22 after passing through the discharge passageway 20. More particularly, and according to the particular arrangement shown in FIG. 1, matter contained within the canister body 16 enters the valve stem 14 through an aperture 24 in a side thereof after the valve stem 14 is sufficiently displaced relative to the canister body 16, and then travels through the valve stem 14 toward the discharge orifice 22 within the MDI to be dispersed into an inhalation passageway to be inhaled by a user through a mouthpiece aperture. The discharge passageway 20 and inhalation passageway of the inhaler, which extends from an outlet of the outlet valve member 12 to the mouthpiece aperture, may be referred as a drug delivery tract.

With continued reference to FIG. 1, and in accordance with conventional MDI devices, the discharge passageway 20 leading from the canister body 16 to the discharge orifice 22 generally remains open and exposed to the environment external to the MDI device, such as through the discharge orifice 22 and/or the aperture 24 in the side of the valve stem 14. In this manner, the discharge passageway 20 is susceptible to moisture ingress which can lead to accelerated fouling of the discharge passageway 20, namely, the deposition or accumulation of matter within the discharge passageway 20.

Embodiments disclosed herein are provided to limit or substantially eliminate the deposition or accumulation of matter within a discharge passageway of a metered dose inhaler or other drug delivery device by (i) selectively sealing the discharge passageway when not actively discharging matter therethrough, and/or (ii) exposing the discharge passageway to a desiccant material.

By way of example, FIG. 2A provides a CT scan showing the accumulation of matter within a discharge passageway of a conventional MDI arrangement arising from repeated use thereof, and FIG. 2B provides a CT scan of a comparable discharge passageway provided in connection with features and techniques described herein to limit or substantially eliminate the deposition or accumulation of matter within the discharge passageway. The respective devices shown in FIGS. 2A and 2B were operated under similar environmental conditions (e.g., temperature and relative humidity) and under similar operational parameters to provide a suitable comparison between a conventional MDI (FIG. 2A) and a device constructed in accordance with aspects and techniques disclosed herein (FIG. 2B). As can be appreciated from a review of FIGS. 2A and 2B, the device constructed in accordance with aspects and techniques disclosed herein shows significant improvement in preventing the deposition or accumulation of matter within the discharge passageway, which advantageously helps to ensure the consistent delivery of a desired dose of the aerosolized matter (e.g., consistent shot weight).

Figure 3A:
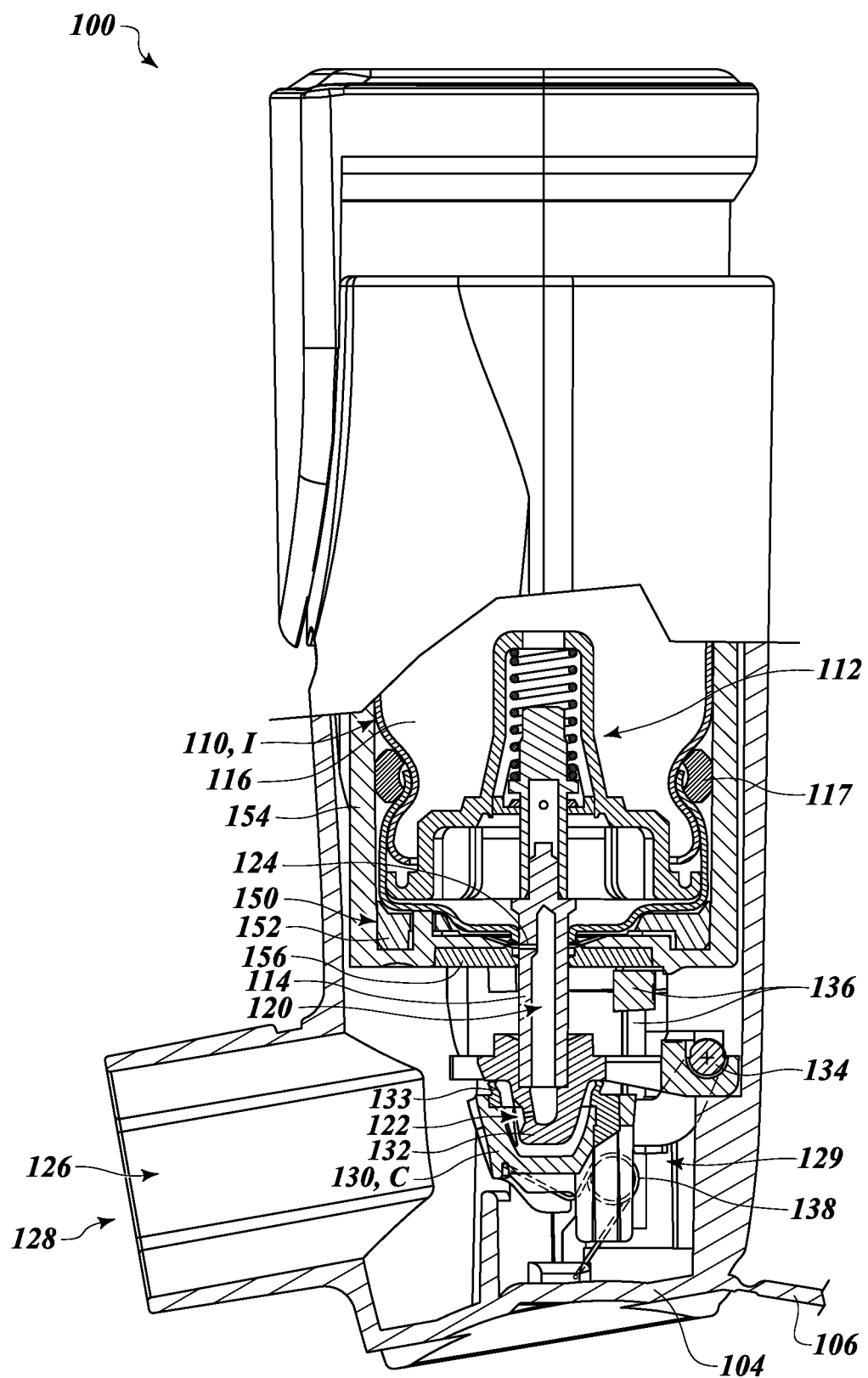
FIG. 3A is a side view of the aerosol delivery unit of FIG. 3 with a portion thereof in cross-section, showing the unit in a standby or storage configuration in which the discharge passageway is sealed from the external environment and also exposed to a desiccant material.
Figure 3B:
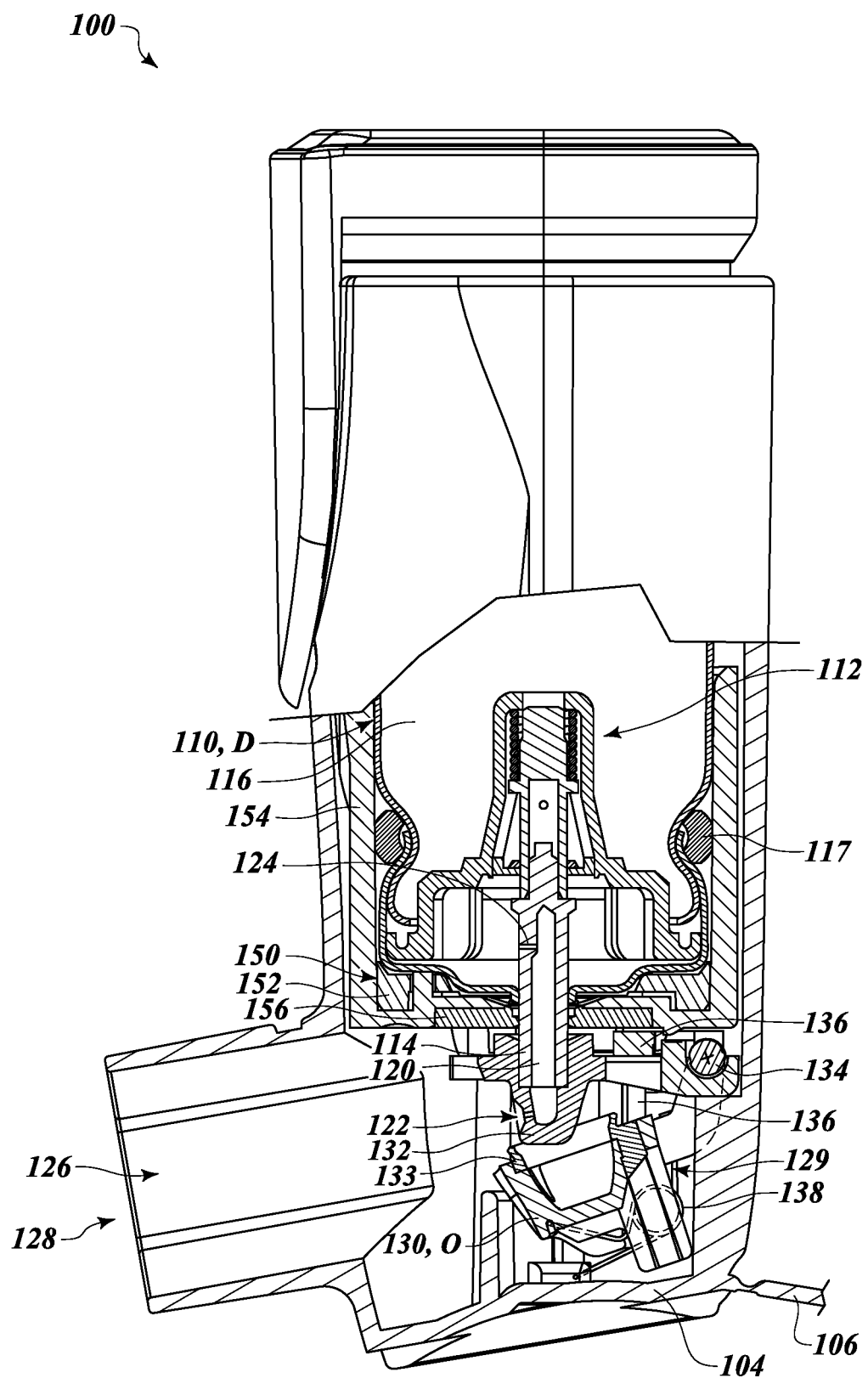
FIG. 3B is a side view of the aerosol delivery unit of FIG. 3 with a portion thereof illustrated in cross-section, showing the unit in a discharge configuration in which the discharge passageway is unsealed to enable aerosolized matter to be discharged from the canister into an inhalation passageway for delivery to a user.
Figure 3C:
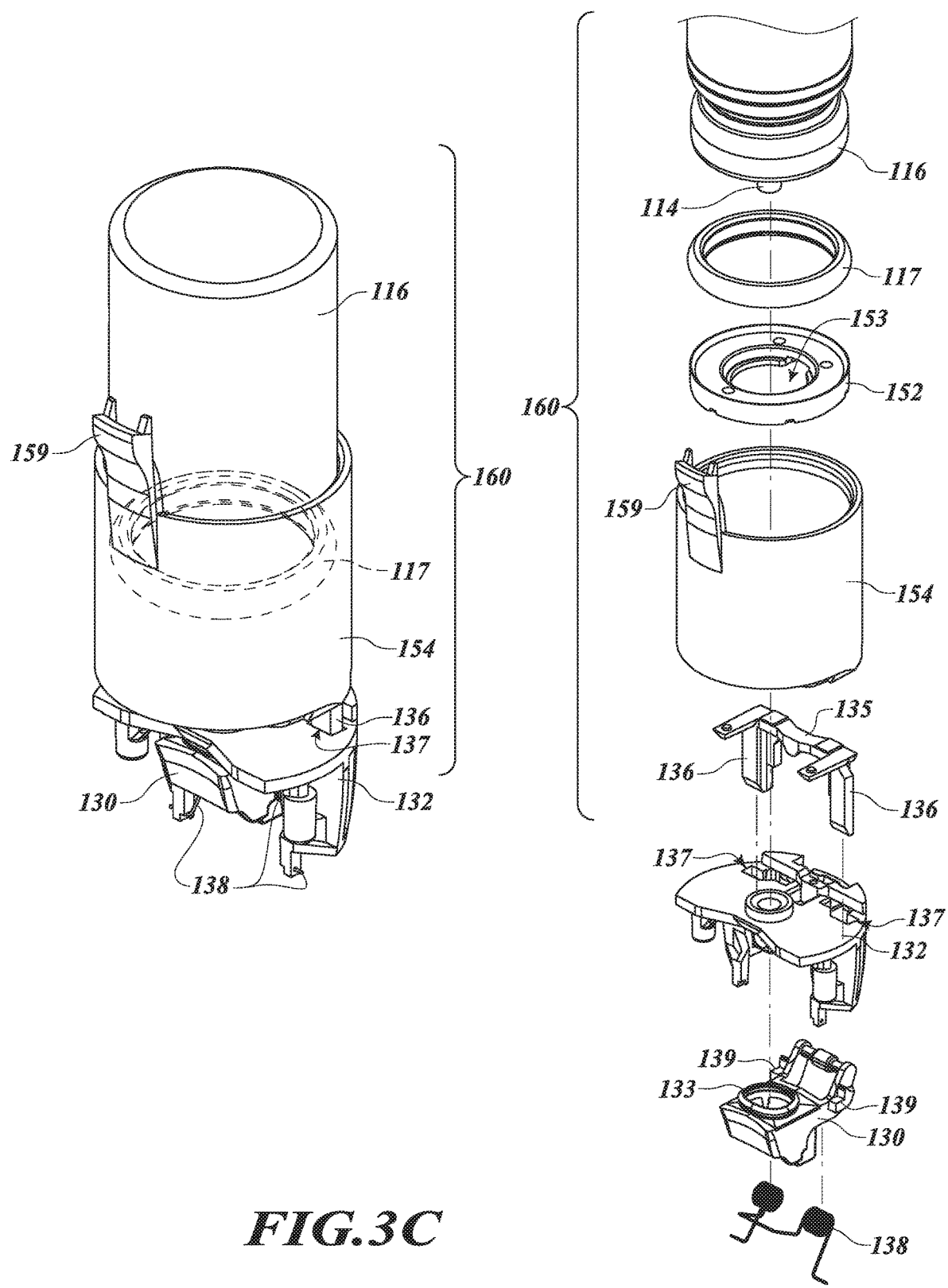
FIG. 3C is an isometric view of some components of the aerosol delivery unit of FIG. 3 shown in collapsed and exploded configurations.
Figure 3D:
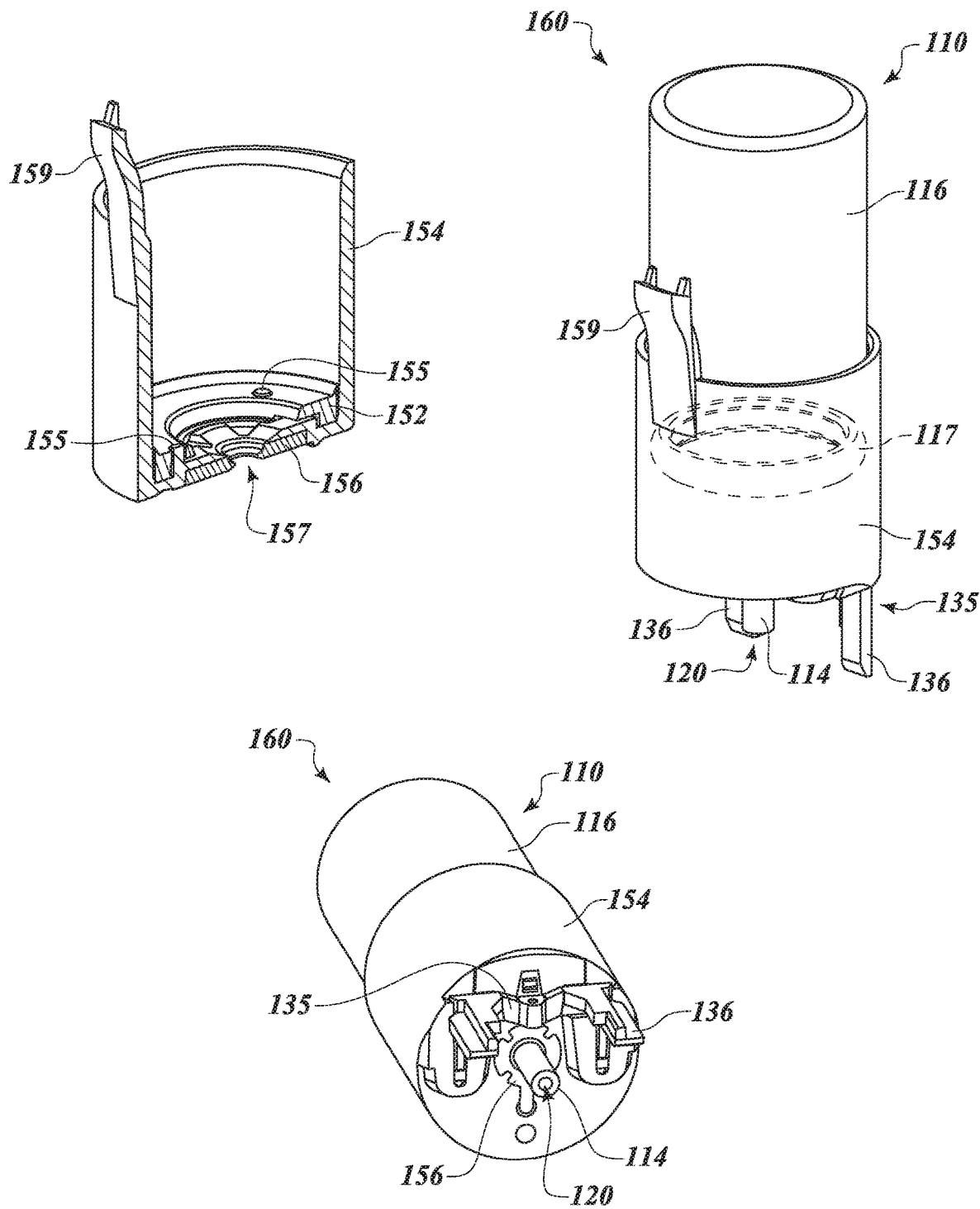
FIG. 3D includes isometric views showing components of a cartridge of the aerosol delivery unit of FIG. 3, which includes a desiccant housing attached to the end of an aerosol canister with a desiccant material received therein.

FIGS. 3, 3A and 3B show one example embodiment of an aerosol delivery unit 100 for selectively delivering a dose of aerosolized matter (referred to generally as a metered dose inhaler or MDI), and FIGS. 3C and 3D show additional details of some of the components thereof.

The aerosol delivery unit 100 includes a base housing 104 and a canister 110 received in the base housing 104, the canister 110 being displaceable from an initial position I, as shown in FIG. 3A, to a discharge position D, as shown in FIG. 3B, for selectively discharging a dose of aerosolized matter for inhalation by a user. The canister 110 comprises a canister body 116, which contains the matter to be discharged, and an outlet valve member 112, which includes a movable valve stem 114 that extends from the canister body 116. The valve stem 114 defines a portion of a discharge passageway 120 extending from the canister body 116 to a discharge orifice 122 provided within the aerosol delivery unit 100, which in turn leads to an inhalation passageway 126 through which the aerosolized matter passes before being discharged through a mouthpiece aperture 128 for inhalation by the user during an inhalation event. The discharge passageway 120 and the inhalation passageway 126 may be collectively referred to as a drug delivery tract. As will be appreciated by those of ordinary skill in the relevant art, when the valve stem 114 is displaced relative to the canister body 116, as shown in FIG. 3B, a metered dose of the matter contained with the canister body 116 will be discharged through the discharge orifice 122 for inhalation by a user via the inhalation passageway 126.

With reference to FIG. 3, the aerosol delivery unit 100 may further include a dose counter assembly 107 secured to an upper under of the canister 110 to provide dose counting functionality and to provide a user interface for depressing the canister 110. The aerosol delivery unit 100 may also include a cap 105 to cover the mouthpiece aperture 128 of the aerosol delivery unit 100 when storing the unit 100. The cap 105 may be completely separable from the base housing 104, or may be coupled to the base housing 104 by a tether 106, which enables the cover 105 to be removed from the mouthpiece aperture 128 while still remaining coupled to the base housing 104.

With reference to FIGS. 3A and 3B, the aerosol delivery unit 100 further includes a seal member 130 movable between a closed position C (FIG. 3A), in which the seal member 130 covers a discharge outlet of the discharge passageway 120, namely, discharge orifice 122, in order to isolate the discharge passageway 120 from the inhalation passageway 126, and an open position O (FIG. 3B), in which the discharge outlet, namely, discharge orifice 122, is in fluid communication with the inhalation passageway 126 to allow the aerosolized matter to pass from the discharge passageway 120 into the inhalation passageway 126 without obstruction for delivery to a user through the mouthpiece aperture 128.

In some instances, including the example embodiment shown in FIGS. 3A and 3B, the seal member 130 may be arranged or otherwise configured relative to the canister 110 to move in direct correlation with movement of the canister 110 from the initial position I, as shown in FIG. 3A, to the discharge position D, shown in FIG. 3B. For example, as shown in the example embodiment of FIGS. 3A and 3B, a seal assembly 129 may be provided and may include a static nozzle block 132 (also referred to herein as a valve stem block) and the seal member 130. The nozzle block 132 may receive the valve stem 114 of the canister 110 and may define a portion of the discharge passageway 120. The seal member 130 may engage or interface with the nozzle block 132 when the seal member 130 is in the closed position C to isolate the discharge passageway 120 from the inhalation passageway 126. The seal member 130 may include a separate or integral seal device 133 to interface with the nozzle block 132. In some instances, the seal device 133 may be formed as an integral portion of the seal member 130 via a multi-shot injection process. In other instances, the seal device 133 may be a distinct feature of a unitary seal member 130, such as a bead or a ridge that provides a sealing edge that may engage the nozzle block 132 when the seal member 130 is in the closed position C. In other instances, the nozzle block 132 may include a separate or integral seal device to interface with the seal member 130. In such instances, the seal device may be formed as an integral portion of the nozzle block 132 via a multi-discharge passageway shot injection process, or the seal device may be a distinct feature of a unitary nozzle block 132, such as a bead or a ridge that provides a sealing edge that may be engaged by the seal member 130 in the closed position C. As shown in the example embodiment of FIGS. 3A and 3B, the seal member 130 may be provide in a cup-like form which cups the nozzle block 132 or a portion of the nozzle block 132 that includes the discharge orifice 122. In other instances, the seal member 130 may take on different forms such as, for example, a planar sealing element (e.g., rotating flap), a ball seal or a movable gate structure.

A seal actuator structure 136 (e.g., push rod) coupled to or otherwise provided on the canister body 116 may be arranged to act on the seal member 130 to transition the seal member 130 to the open position O, as shown in FIG. 3B. In this manner, moving the canister 110 to discharge the aerosolized matter also results in displacing the seal member 130 to open the discharge passageway 120. The seal member 130 of the example embodiment is configured such that it moves away from the nozzle block 132 out of the discharge path emanating from the discharge orifice 122 before the outlet valve member 112 releases material from the canister 110 through the discharge passageway 120 so as to not obstruct the flow of aerosolized matter through the discharge orifice 122 into the inhalation passageway 126. In some instances, for example, the seal member 130 will be entirely outside of a reference cylinder that is aligned with a central axis defined by the discharge orifice 122 and that is tangent to an outlet of the discharge passageway 120. In some instances, the seal member 130 will be entirely outside of a reference cone having an opening angle of 90° that is aligned with a central axis defined by the discharge orifice 122 and that is tangent to an outlet of the discharge orifice 122.

Figure 17:
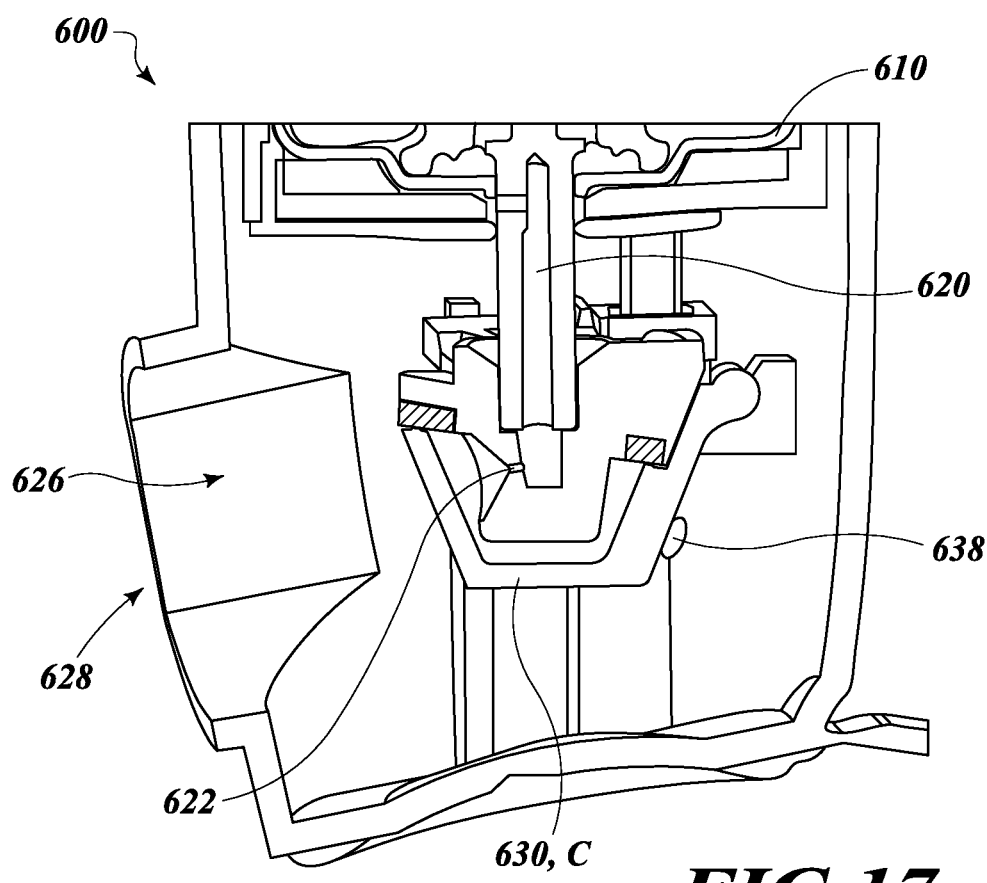
FIG. 17 is a partial cross-sectional side view of an aerosol delivery unit, according to another example embodiment, showing the unit in a standby or storage configuration in which the discharge passageway is sealed from the external environment and also exposed to a desiccant material.
Figure 18:
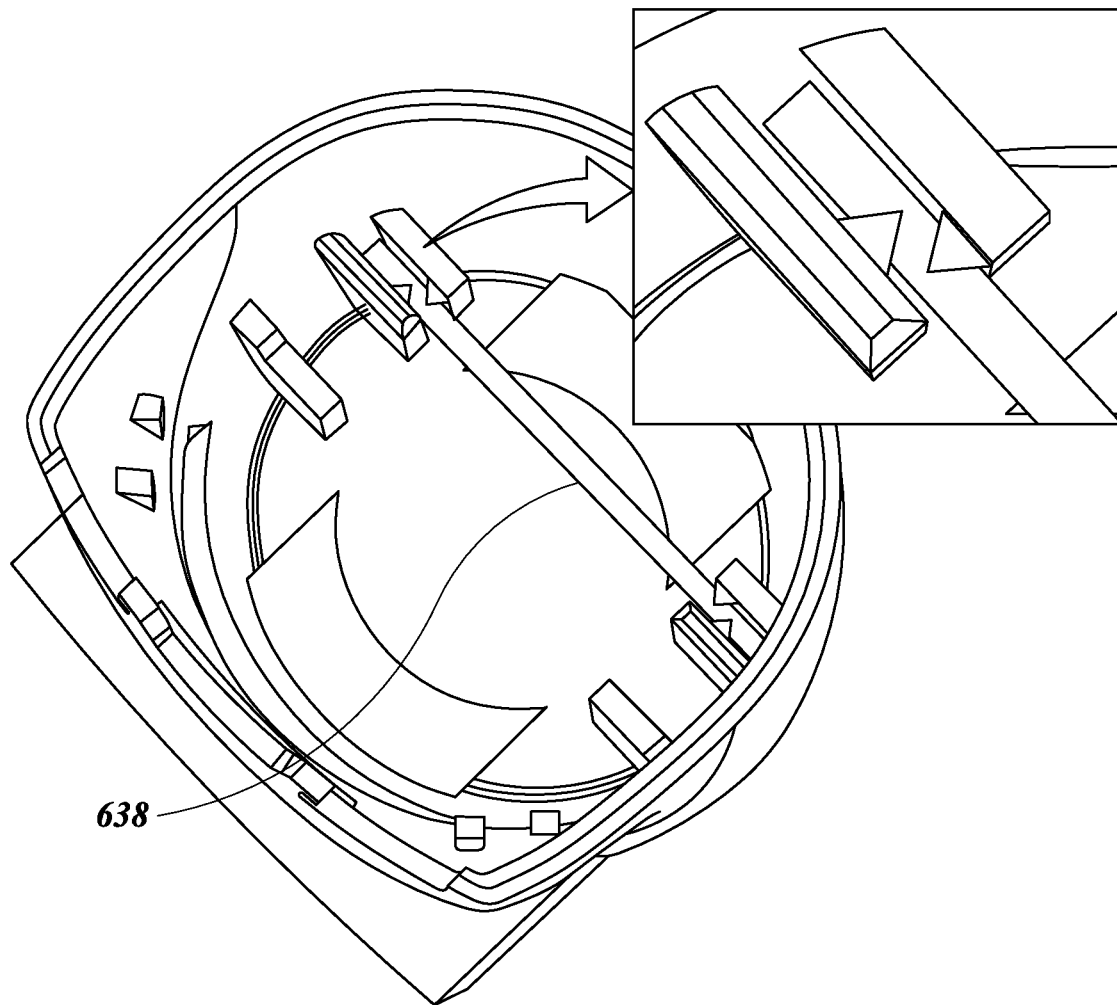
FIG. 18 is a top perspective view of a portion of the aerosol delivery unit of FIG. 17 showing additional details of a biasing element, in the form of a resilient band, for assisting in sealing the discharge passageway, along with depicting alternate band geometry.

In accordance with the example embodiment of FIGS. 3A and 3B, the discharge orifice 122 and a portion of the discharge passageway 120 (e.g., a sump portion) is provided in the nozzle block 132. According to the example embodiment shown in FIGS. 3A and 3B, the nozzle block 132 is supported in a fixed manner within the base housing 104 and is configured to receive the discharge end of the valve stem 114 that extends from the canister 110. In other instances, the nozzle block 132 may be formed integrally with the base housing 104. In still other instances, the nozzle block 132 and the seal member 130 may be portions of a unitary component having a living hinge or other joint to enable the seal member 130 to move relative to the nozzle block 132.

The seal member 130 may be biased toward the closed position C to engage the stem block 132 by a return spring 138 (e.g., torsional spring, coil spring, leaf spring) or other biasing element (e.g., resilient band, elastically deformable member). In this manner, the seal member 130 may be held securely in the closed position C until acted upon in coordination with the movement of the canister 110 from the initial position I (FIG. 3A) to the discharge position D (FIG. 3B). In some instances, the return spring 138 may be captured with the aerosol delivery unit 100 to be held captive within the unit 100 upon failure of the return spring 138 or dislodgement of the return spring 138 from its intended installation position.

Although the seal member 130 and the stem block 132 are shown in the example embodiment as two separate components that are connected by a hinge arrangement 134 to interface with each other to selectively seal the discharge passageway 120, it is appreciated that various other sealing arrangements may be provided in lieu of the illustrated arrangement. For example, as described above, the stem block 132 and the seal member 130 may be portions of a unitary component having a living hinge or other joint to enable the seal member 130 to move relative to the nozzle block 132.

FIGS. 17 and 18 show another example embodiment of an aerosol delivery unit 600 for selectively delivering a dose of aerosolized matter (referred to generally as a metered dose inhaler or MDI). The aerosol delivery unit similarly includes a seal member 630 movable between a closed position C (FIG. 17), in which the seal member 630 covers a discharge outlet of the discharge passageway 620, namely, discharge orifice 622, in order to isolate the discharge passageway 620 from the inhalation passageway 626, and an open position O (not shown), in which the discharge outlet, namely, discharge orifice 622, is in fluid communication with the inhalation passageway 626 to allow the aerosolized matter to pass from the discharge passageway 620 into the inhalation passageway 626 without obstruction for delivery to a user through the mouthpiece aperture 628. According to the embodiment illustrated in FIGS. 17 and 18, at least a portion of the seal member 630 may be biased toward the closed position C by a biasing element 638, such as, for example, a resilient band, which contacts a portion of the seal member 630 and urges it toward the closed position C throughout operation. One of ordinary skill in the relevant art will appreciate that the biasing element 638 may deform elastically during actuation of the canister 610 and displacement of the seal member 630 to an open position and that the magnitude of the biasing force may vary throughout movement of the seal member 630, increasing with the amount that the biasing element 638 is displaced. As shown in the example embodiment of FIGS. 17 and 18, the biasing element 638, may be provided in the form of a resilient band that spans across and is in contact with or adjacent to a back side of the seal member 630.

With reference back to FIGS. 3A and 3B, the aerosol delivery unit 100 further includes a desiccant chamber 150 containing a desiccant material 152 that is in fluid communication with the discharge passageway 120 at least when the aerosol delivery unit 100 is in a storage configuration and not actively discharging aerosolized matter. For example, in accordance with the example embodiment shown in FIGS. 3A and 3B, the desiccant chamber 150 is provided at an end of the canister 110 between a lower end of the canister body 116 and a separate desiccant housing 154 and stem seal 156 that are coupled to the end of the canister 110. The desiccant material 152 may be provided in disc form and may include a central aperture through which the valve stem 114 of the canister 110 passes. The stem seal 156 may be an annular seal formed integrally with the desiccant housing 154, such as, for example, via a multi-shot injection molding process, or may otherwise be provided as a separate seal component coupled to the desiccant housing 154. In some instances, the stem seal 156 may be provided as a bellows type seal that is secured between the valve stem 114 and the desiccant housing to provide a desiccant chamber 150 having a volume that varies as the stem seal 156 is deformed as the canister 110 is displaced during an inhalation event. In other instances, such as the example embodiment shown in FIGS. 3A and 3B, the desiccant chamber 150 may have a fixed volume.

As can be appreciated from FIG. 3A, the desiccant material 152 within the desiccant chamber 150 is in fluid communication with the discharge passageway 120 through the aperture 124 in the side of the valve stem 114 that is otherwise used to pass the matter contained in the canister body 116 toward the discharge orifice 122 when the valve stem 114 is displaced during an inhalation event. In this manner, the discharge passageway 120 remains exposed to the desiccant material 152 when the canister 110 is in the initial position I, such as when storing the unit 100. In some instances, the desiccant material may be sufficient to keep the discharge passageway dry (e.g., <25% RH) between uses for substantially the entire product life of the canister of material to be discharged.

Advantageously, the desiccant housing 154 may be coupled to the end or collar of the canister 110 to form a cartridge 160 therewith that is readily removable from the base housing 104. In this manner, the desiccant housing 154 and canister 110 may be easily removed from the base housing 104 to replace the canister 110 when depleted and/or to replace the desiccant material 152 as desired. The desiccant housing 154 may be coupled to the end or collar of the canister 110 via a resilient band, clips, detents or other fastening devices or techniques, including friction fit or interference fit arrangements. Although the desiccant chamber 150 is shown in the example embodiment of FIGS. 3A and 3B as being coupled to a lower end or collar of the canister 110, it is appreciated that in other embodiments a desiccant chamber may be provided in a separate desiccant housing that is coupled to the base housing 104 separate from the canister 110, the desiccant chamber may be formed integrally in the base housing itself, or the desiccant chamber may be provided in a separate component that is attached to the base housing 104, such as a mouthpiece cap, as shown and described in greater detail elsewhere herein. In addition, the desiccant material may be provided in a variety of different forms, such as gel form, powder form, granular form or molded form, and may consist of or comprise different materials, such as silica, activated charcoal, calcium sulfate or calcium chloride. Still further, it is appreciated that in some embodiments a desiccant chamber and the associated desiccant may be omitted altogether.

As previously described, the desiccant housing 154 may be coupled to the end or collar of the canister 110 to form a cartridge 160 that is installable in the base housing 104 to engage the stem block 132 and operate in conjunction with the seal member 130 to provide some of the functionality described herein. Further details of the components of the cartridge 160, stem block 132 and seal member 130 are shown in FIGS. 3C and 3D. As shown in FIGS. 3C and 3D, the desiccant housing 154 may form a cup-like structure with a generally cylindrical sidewall that is sized and shaped to receive a lower end of the canister 110. The desiccant material 152 may be provided in a molded form and may have a generally annular shape. The desiccant material 152 may be positioned in a lower end of the desiccant housing 154. The desiccant housing 154 may include one or more locating or coupling features 155 to assist in joining or otherwise positioning the desiccant material 152 within the desiccant housing 154. According to the example embodiment shown in FIGS. 3C and 3D, the desiccant material 152 is shaped so as to not obstruct a valve stem aperture 157 (FIG. 3D) provided in the desiccant housing 154 through which the valve stem 114 of the canister 110 is received. More particularly, the valve stem aperture 157 is provided in stem seal 156, which may be formed integrally with the desiccant housing 154, such as, for example, via a multi-shot injection molding process, and the desiccant material 152 has an annular form with a central aperture 153 to provide the valve stem 114 of the canister 110 with unimpeded access to the valve stem aperture 157 of the stem seal 156 of the desiccant housing 154.

With continued reference to FIGS. 3C and 3D, a canister seal 117 may be positioned around the canister body 116, such as around a lower neck portion thereof, to provide a resilient member between the canister body 116 and the desiccant housing 154 which may be compressed when the canister 110 and the desiccant housing 154 are coupled together. The canister seal 117 may provide a seal location to assist in isolating the desiccant chamber 150 (FIGS. 3A and 3B) when the aerosol delivery unit 100 is fully assembled and in preventing the ingress of moisture into said desiccant chamber 150 other than through the discharge passageway 120. In a similar manner, the stem seal 156 may provide a seal location to assist in isolating the desiccant chamber 150 (FIGS. 3A and 3B) when the aerosol delivery unit 100 is fully assembled and in preventing the ingress of moisture into said desiccant chamber 150 other than through the discharge passageway 120. In this manner, the desiccant chamber 150 is effectively isolated from the external environment apart from the discharge passageway 120, which may be exposed to the external environment when discharging medicament or, in the case of a unit in which the seal member 130 is omitted, when the inhalation passageway 120 is otherwise exposed to the external environment, such as when the mouthpiece cap 105 is removed from the base housing 104 of the aerosol delivery unit 100.

With the canister 100 loaded in the desiccant housing 154, the valve stem 114 protrudes from a lower end thereof to be subsequently received in the nozzle block 132 provided in the base housing 104. The desiccant housing 154 may further include a latch 159, detent mechanism or other coupling arrangement for removably securing the cartridge 160 within the base housing 104. For example, the desiccant housing 154 may include a resilient latch 159 that is configured to engage a latching aperture (not shown) in the base housing 104 to assist in retaining the cartridge 160 within the base housing 104. The latch 159 may be depressed to selectively remove the cartridge 160 from the base housing 104 as needed or desired. Other features may be included in the desiccant housing 154 and/or the base housing 104 to assist in locating the cartridge 160 in the base housing 104 and in guiding the cartridge 160 relative to the base housing 104 as it is depressed during use to actuate the valve stem 114 and release a dose of material.

With continued reference to FIGS. 3C and 3D, the cartridge 160 may include a seal actuator component 135 coupled to or integrated with a lower end of the desiccant housing 154 to provide the seal actuator structure 136 (e.g., push rods) which acts on the seal member 130 during use to transition the seal member 130 to the open position O, as shown in FIG. 3B. The seal actuator component 135 may be removably coupled to the lower end of the desiccant housing 154 and may be configured such that the seal actuator structure 136 extends through one or more corresponding apertures 137 in the nozzle block 132 to assist in guiding and supporting the seal actuator structure 136 as it acts on the seal member 130 to displace the seal member 130 during the inhalation event. For example, according to the illustrated embodiment in FIGS. 3 through 3D, the seal actuator structure 136 comprises a pair of push rods that extend through corresponding apertures 137 in the nozzle block 132 and are positioned to engage lugs 139 on the seal member 130 for driving the seal member 130 to the open position O as the canister 110 is depressed. In some instances, the push rods (or other seal actuator structure 136) are configured to move past the lugs 139 before reaching the end of their travel such that the push rods hold the seal member 130 open at the end of their travel without imparting a downward force on the seal member 130. Although the seal actuator structure 136 is shown and described in the example embodiment as a pair of push rods, it is appreciated that other structures, including linkage arrangements, may be provided to transform movement of the canister 110 when discharging a dose of the material in the canister 110 to movement of the seal member 130 to uncover the discharge passageway 120.

Figure 4:
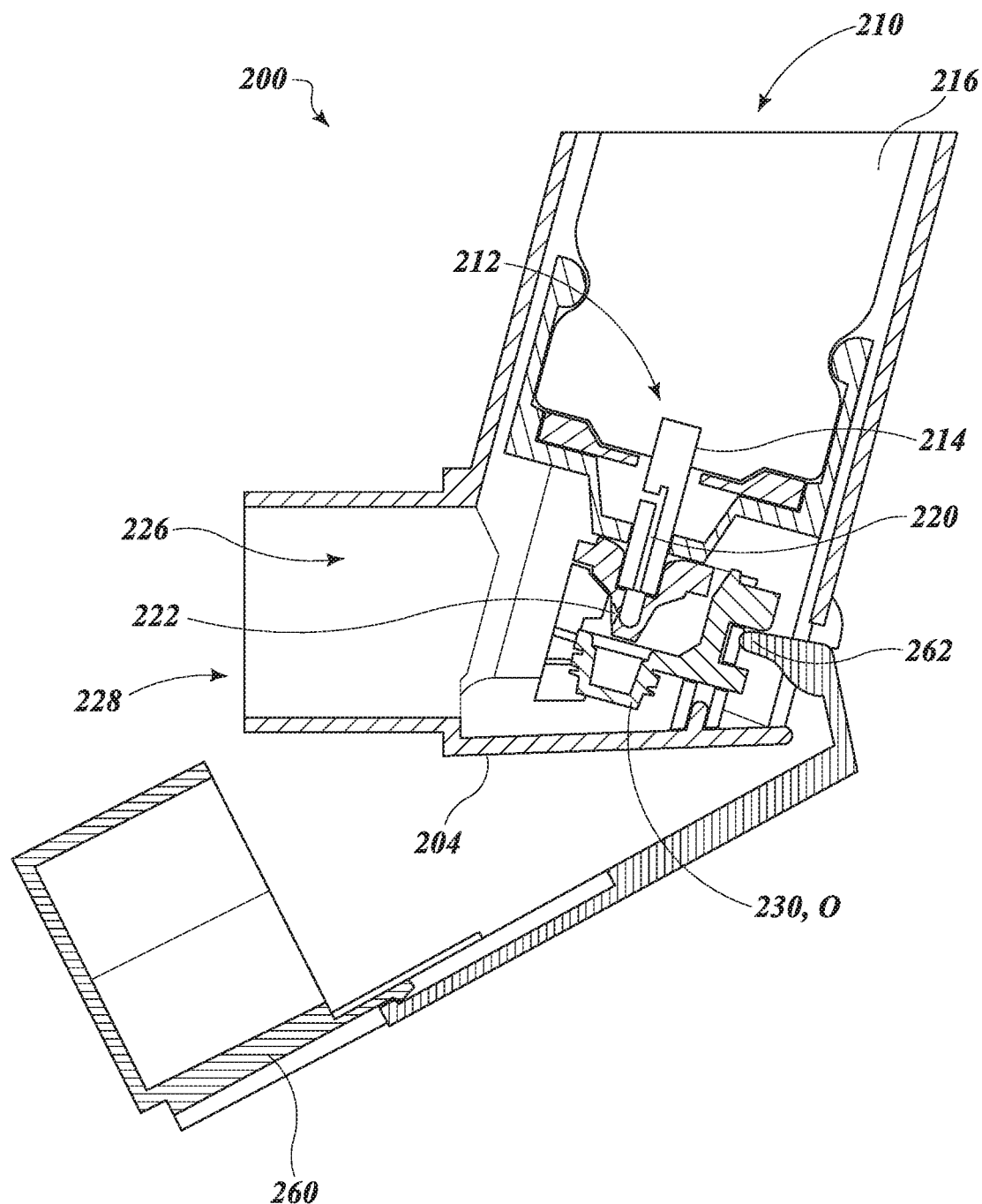
FIG. 4 is a partial cross-sectional side view of an aerosol delivery unit, according to another example embodiment, showing the unit in a discharge configuration in which the discharge passageway is unsealed to enable aerosolized matter to be discharged from the canister into an inhalation passageway for delivery to a user.

FIG. 4 shows another example embodiment of an aerosol delivery unit 200 for selectively delivering a dose of aerosolized matter (referred to generally as a metered dose inhaler or MDI). The aerosol delivery unit 200 similarly includes a base housing 204 and a canister 210 received in the base housing 204, the canister 210 being displaceable from an initial position to a discharge position for selectively discharging a dose of aerosolized matter for inhalation by a user. The canister 210 comprises a canister body 216, which contains the matter to be discharged, and an outlet valve member 212, which includes a movable valve stem 214 that extends from the canister body 216. The valve stem 214 defines a portion of a discharge passageway 220 extending from the canister body 216 to a discharge orifice 222 that is provided within the aerosol delivery unit 200, which in turn leads to an inhalation passageway 226 through which the aerosolized matter passes before being discharged through a mouthpiece aperture 228 for inhalation by the user during an inhalation event.

With continued reference to FIG. 4, the aerosol delivery unit 200 further includes a seal member 230 movable between a closed position (not shown), in which the seal member 230 covers a discharge outlet of the discharge passageway 220, namely, discharge orifice 222, in order to isolate the discharge passageway 220 from the inhalation passageway 226, and an open position O, as shown in FIG. 4, in which the discharge outlet, namely, discharge orifice 222, is in fluid communication with the inhalation passageway 226 to allow the aerosolized matter to pass from the discharge passageway 220 into the inhalation passageway 226 without obstruction for delivery to a user through the mouthpiece aperture 228.

In some instances, including the example embodiment shown in FIG. 4, the aerosol delivery unit 200 may include a mouthpiece cap 260 and the seal member 230 may be arranged or otherwise configured relative to the mouthpiece cap 260 to move in coordination with movement of the mouthpiece cap 260. For example, as shown in the example embodiment of FIG. 4, the seal member 230 may be operatively coupled to a cam portion 262 of the mouthpiece cap 260 such that the seal member 230 is moved away from the closed position toward the open position O as the mouthpiece cap 260 is rotated away from the end of the unit 200 comprising the mouthpiece aperture 228. Conversely, as the mouthpiece cap 260 is rotated back toward the end of the unit 200 comprising the mouthpiece aperture 228, the seal member 230 may be displaced toward the closed position to seal the discharge passageway 220. In this manner, the discharge orifice 222 may be uncovered as a user prepares to take a dose of the aerosolized matter by removing the mouthpiece cap 260 and rotating it away from the end of the unit 200 containing the mouthpiece aperture 228, and then covered again as the user replaces the mouthpiece cap 260 to store the unit 200 for future use.

Figure 5:
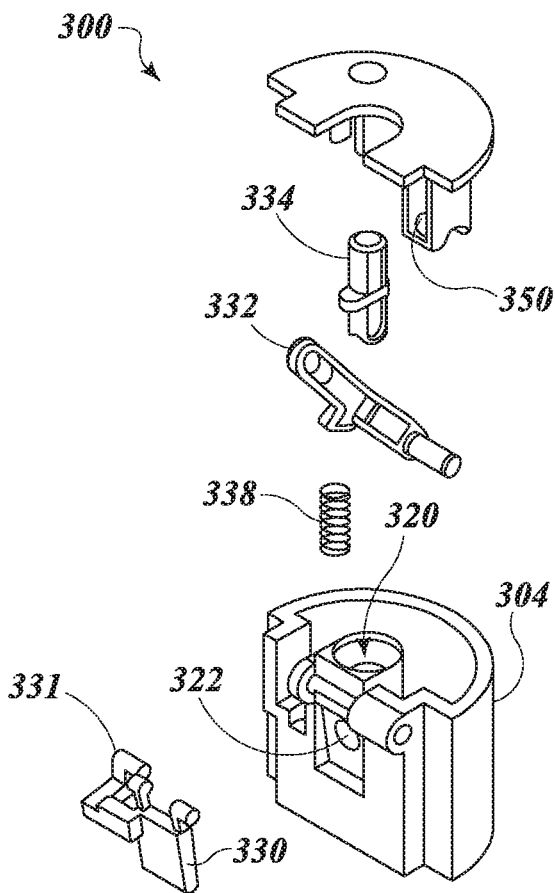
FIG. 5 is an exploded isometric view of a portion of an aerosol delivery unit, according to another example embodiment.
Figure 6:
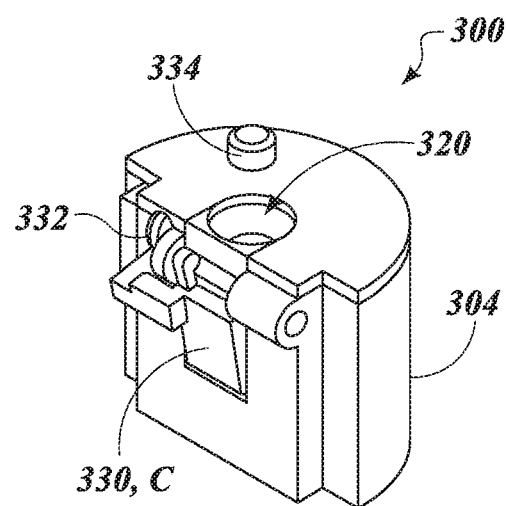
FIG. 6 is a collapsed isometric view of the portion of the aerosol delivery unit of FIG. 5, showing a seal member thereof in a closed position over a discharge orifice through which aerosolized matter is discharged during use.
Figure 7:
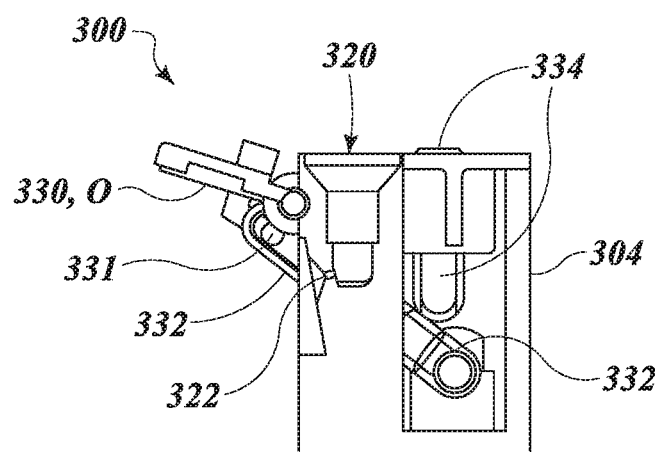
FIG. 7 is a cross-sectional side view of the portion of the aerosol delivery unit shown in FIGS. 5 and 6, showing the seal member in an open position in which an aerosol discharge path through the discharge orifice is not obstructed by the seal member.

FIGS. 5 through 7 show a valve stem block 300 of another example embodiment of an aerosol delivery unit for selectively delivering a dose of aerosolized matter. The valve stem block 300 may be positioned within a base housing of the aerosol delivery unit and may be configured to receive the valve stem of a conventional canister for a metered dose inhaler. FIGS. 5 and 6 show the valve stem block 300 in an exploded view and a collapsed view, respectively, and FIG. 7 provides a cross-sectional side view thereof.

As shown in FIGS. 5 through 7, a seal member 330 is operatively coupled to a valve stem block housing 304 to move between a closed position C, as shown in FIG. 6, and an open position O, as shown in FIG. 7. A linkage 332 is operatively coupled to the valve stem block housing 304 and the seal member 330 to assist in moving the seal member 330 between the closed position C (FIG. 6) and the open position O (FIG. 7). According to the example embodiment of the valve stem block 300 of FIGS. 5 through 7, the seal member 330 is configured to rotate or flip up to uncover a discharge orifice 322 formed in the valve stem block housing 304 in response to the canister (not shown) pressing upon a push member 334 extending from the stem block housing 304 when the canister is depressed to a discharge position, the push member 334 in turn pressing upon the linkage 332 to cause the seal member 330 to rotate as the linkage 332 acts upon a cam member 331 of the seal member 330. When the canister returns to its initial position, a return spring 338 or other bias member urges the linkage 332 to urge the seal member 330 back into the closed position C (FIG. 6). In this manner, the seal member 330 is held in a normally closed position C (FIG. 6) and moved to the open position O (FIG. 7) only when the canister is depressed to deliver a dose of the aerosolized matter.

Advantageously, the linkage 332 is arranged to convert or amplify a relatively small vertical displacement associated with a stroke of the canister to a relatively large rotational movement of the seal member 330. Furthermore, the linkage 332 is configured to move the seal member 330 completely out of the flow path of the aerosolized matter before the matter is discharged through the discharge orifice 322 at the end of the discharge passageway 320. In this manner, at least a portion of the seal member 330 may move a distance greater than a travel distance of the stroke of the canister.

With continued reference to FIGS. 5 through 7, the valve stem block housing 304 of the valve stem block 300 may further include or define a desiccant chamber 350 containing a desiccant material (not shown) which is in fluid communication with the discharge passageway 320 passing through the stem block housing 304. As such, the valve stem block 300 may comprise a self-contained assembly sufficient to selectively isolate the discharge passageway 320 and remove moisture therefrom when a canister is loaded therein and not actively discharging aerosolized matter. In some instances, the desiccant material may be sufficient to keep the discharge passageway dry (e.g., <25% RH) between uses for substantially the entire product life of the canister of material to be discharged. According to this embodiment, the desiccant material is exposed to a downstream end of the discharge passageway 320 rather than an upstream end through the aperture in the side of the valve stem of the canister that is otherwise used to pass the matter contained in the canister body toward the discharge orifice 322 when the valve stem is displaced during an inhalation event.

FIGS. 8 through 9B show a similar valve stem block 400 of another example embodiment of an aerosol delivery unit for selectively delivering a dose of aerosolized matter. The valve stem block 400 may be positioned within a base housing of the aerosol delivery unit and may be configured to receive the valve stem of a conventional canister for a metered dose inhaler. FIG. 8 provides a skewed isometric view of a portion of the valve stem block 400 and FIGS. 9A and 9B provide cross-sectional side views of the valve stem block 400 with a seal member 430 thereof in a closed position C and an open position O, respectively.

As shown in FIGS. 8 through 9B, the seal member 430 is operatively coupled to a valve stem block housing 404 to move between the closed position C, as shown in FIG. 9A, and the open position O, as shown in FIG. 9B. A linkage 432 is operatively coupled to the valve stem block housing 404 and the seal member 430 to assist in moving the seal member 430 between the closed position C (FIG. 9A) and the open position (FIG. 9B). According to the example embodiment of FIGS. 8 through 9B, the seal member 430 is configured to rotate or flip up to uncover a discharge orifice 422 (FIG. 8) formed in the valve stem block housing 404 in response to the canister (not shown) pressing upon a push member 434 extending from the stem block housing 404 when the canister is depressed to a discharge position, the push member 434 in turn pressing upon the linkage 432 to cause the seal member 430 to rotate as the linkage 432 acts upon a cam member 431 of the seal member 430. When the canister returns to its initial position, a return spring (not visible) or other bias member urges the linkage 432 to urge the seal member 430 back into the closed position C (FIG. 9A). In this manner, the seal member 430 is held in a normally closed position C (FIG. 9A) and moved to the open position O (FIG. 9B) only when the canister is depressed to deliver a dose of the aerosolized matter. As shown in FIG. 8, the discharge orifice 422 may be encircled by a ridge 423 or other feature that may interface with the seal member 430 in the closed position C to assist in creating and maintaining a seal that isolates the upstream discharge passageway 420 from a downstream inhalation passageway (not shown).

The embodiments described above provide a few examples of various seal member arrangements and desiccant chamber arrangements suitable for selectively isolating the discharge passageway of a metered dose inhaler or other drug delivery device and for removing moisture from said isolated passageway. It is appreciated, however, that various other seal member arrangements and desiccant chamber arrangements may be utilized to provide the same or similar functionality.

Figure 10:
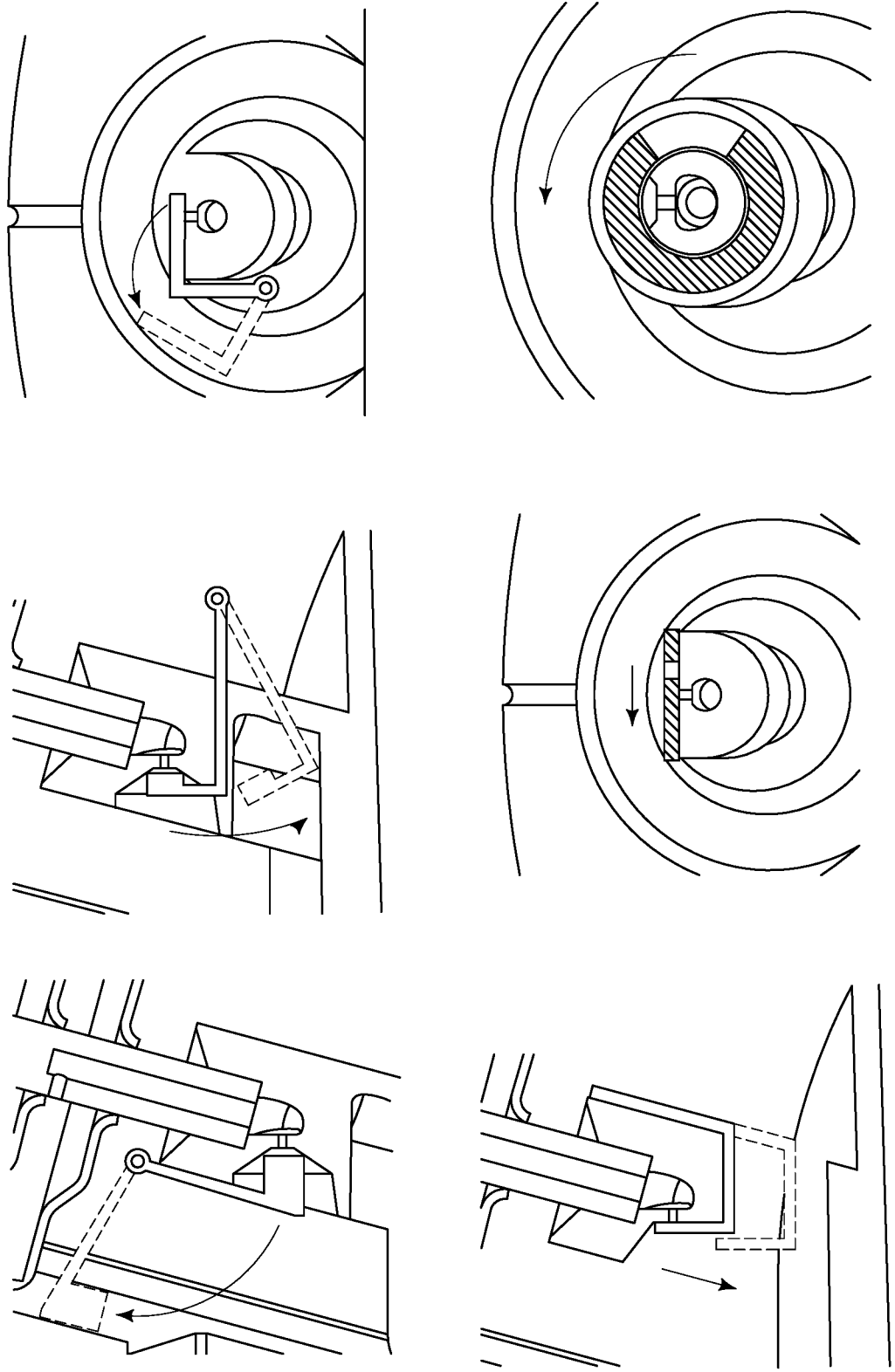
FIG. 10 provides schematic diagrams of various seal member arrangements that may be used to selectively isolate a discharge passageway of an aerosol delivery unit.

For example, FIG. 10 provides schematic diagrams of various seal member arrangements that may be used to selectively isolate a discharge passageway of an aerosol delivery unit, including arrangements in which the seal member may pivot, slide or rotate between a closed position and an open position to cover the discharge orifice of the aerosol delivery unit and isolate a discharge passageway thereof.

A desiccant chamber may also be provided in any suitable location and manner to communicate with the isolated discharge passageway of the aerosol delivery unit. This may include a chamber formed or otherwise coupled to the end of the canister, such as, for example, the embodiment shown in FIGS. 3A and 3B.

Figure 11:
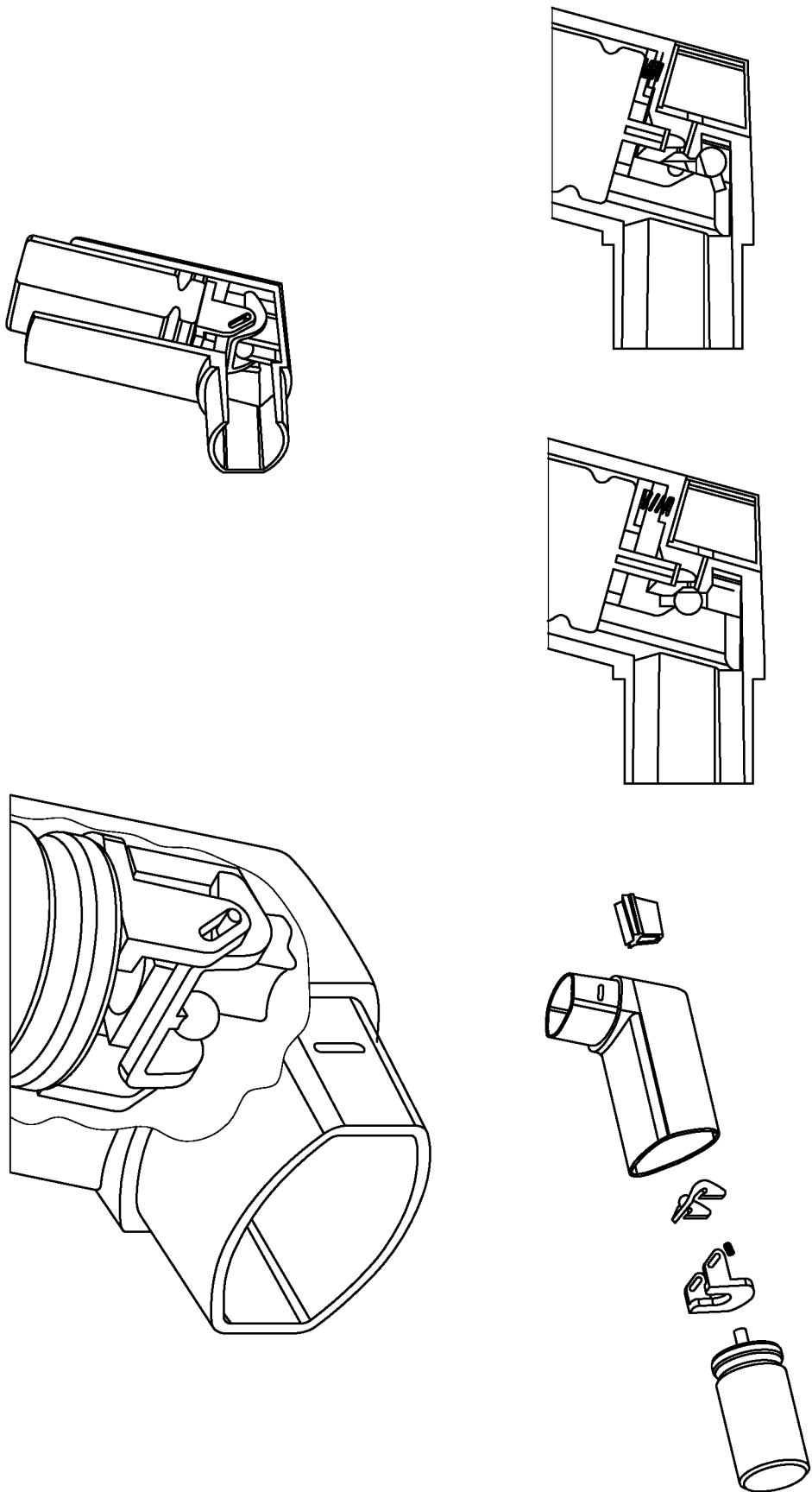
FIG. 11 shows another example embodiment of an aerosol delivery unit having a movable ball seal and a separate desiccant housing.
Figure 12:
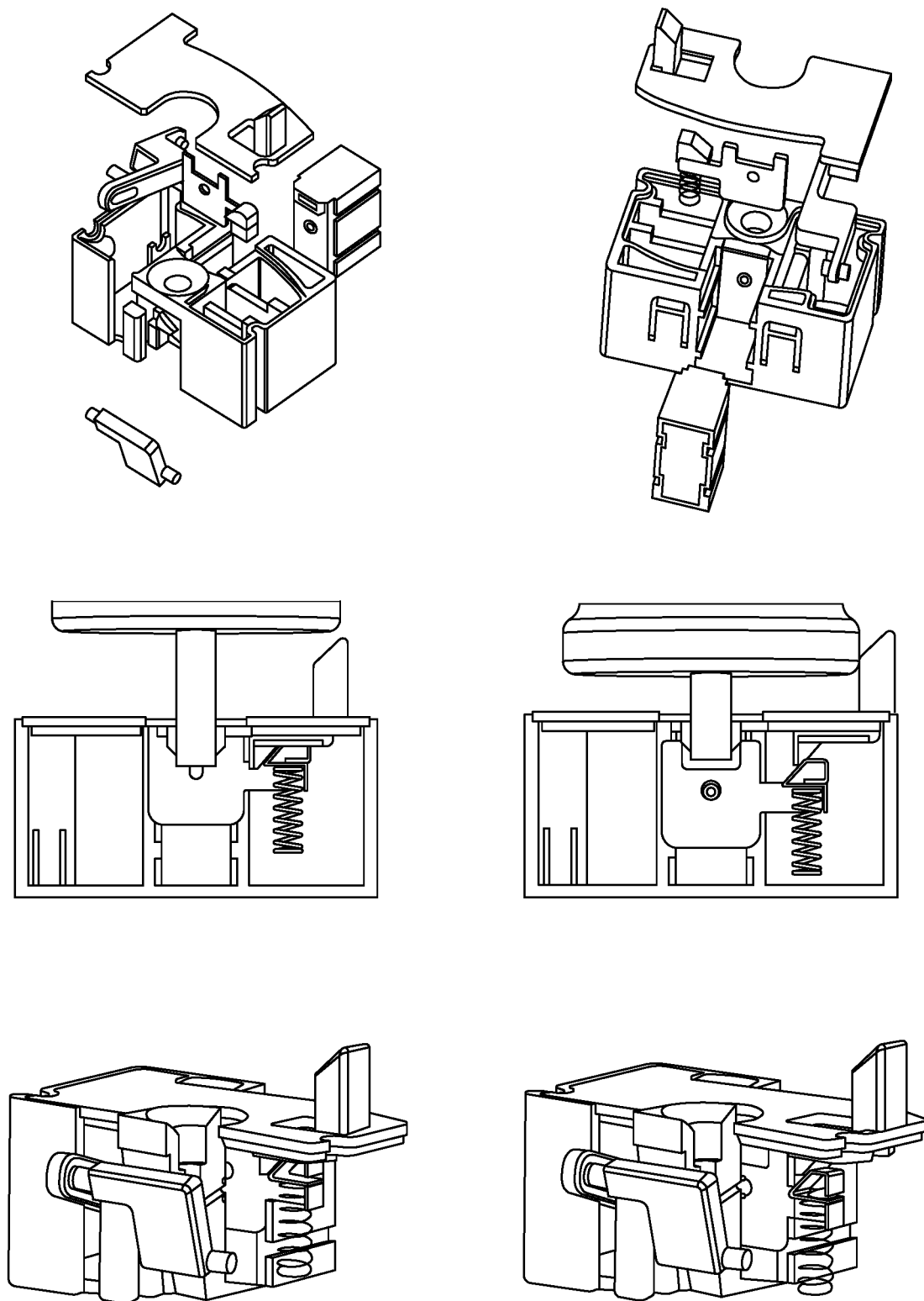
FIG. 12 shows another example embodiment of an aerosol delivery unit having a movable gate element to selectively close off a desiccant chamber thereof.

In other instances, a desiccant housing may be provided within the base housing of the aerosol delivery unit and may be configured to remain within the base housing when the canister is removed therefrom, such as may be the case when installing a replacement canister, or cleaning the unit. For instance, FIG. 11 illustrates one example embodiment of an aerosol delivery unit having a desiccant housing located in a base housing of the aerosol delivery unit separate from the canister, which is in fluid communication with the discharge passageway when the aerosol delivery unit is not actively discharging medicament or other matter. FIG. 12 illustrates yet another example embodiment of an aerosol delivery unit having a desiccant housing located in the base housing of the aerosol delivery unit separate from the canister. According to the embodiment of FIG. 12, the aerosol delivery unit further includes a movable gate arrangement for selectively isolating the desiccant chamber from the discharge passageway when the canister is removed from the unit. In this manner, the desiccant chamber may be sealed when the canister is removed, such as may be the case when cleaning the aerosol delivery unit.

Figure 13:
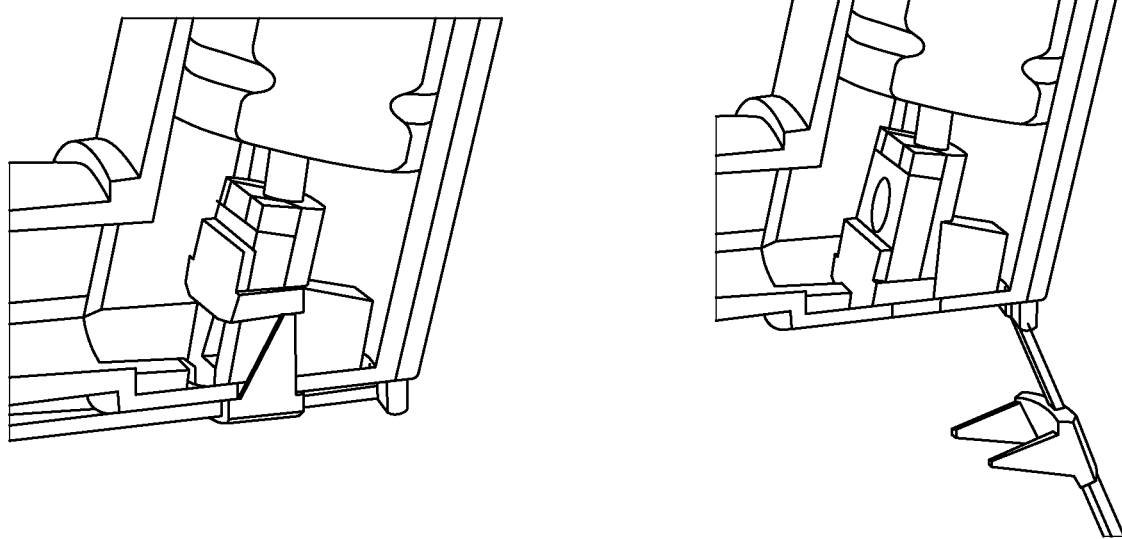
FIG. 13 shows another example embodiment of an aerosol delivery unit having a desiccant chamber formed integrally with a housing thereof, and including a manipulable mouthpiece cap that is configured to control movement of a seal member for selectively isolating a discharge passageway of the unit.
Figure 14:
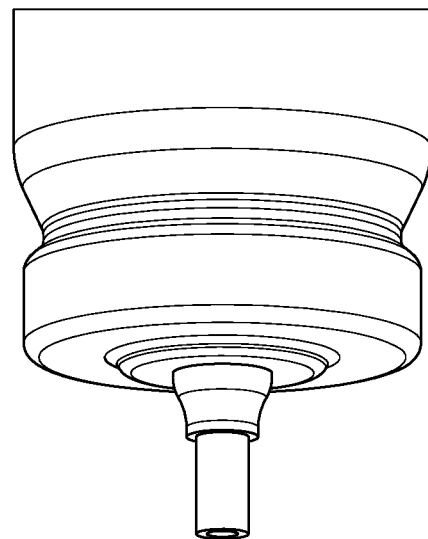
FIG. 14 shows a supplemental seal member that is used to block an aperture in the side of the valve stem of a conventional canister of an MDI when the valve stem is in an expanded or uncompressed position.

In still other embodiments, the base housing itself may include a desiccant housing portion that defines the desiccant chamber. FIG. 13 shows one example embodiment of an aerosol delivery unit having a desiccant chamber formed integrally with the housing thereof. In such instances, a supplemental seal member may be provided to seal the aperture in the side of the valve stem of the canister, which may otherwise be exposed to the external environment when the canister is in its initial position. An example of such a supplemental seal is shown in FIG. 14 encircling a base of the valve stem adjacent the canister body.

Figure 15:
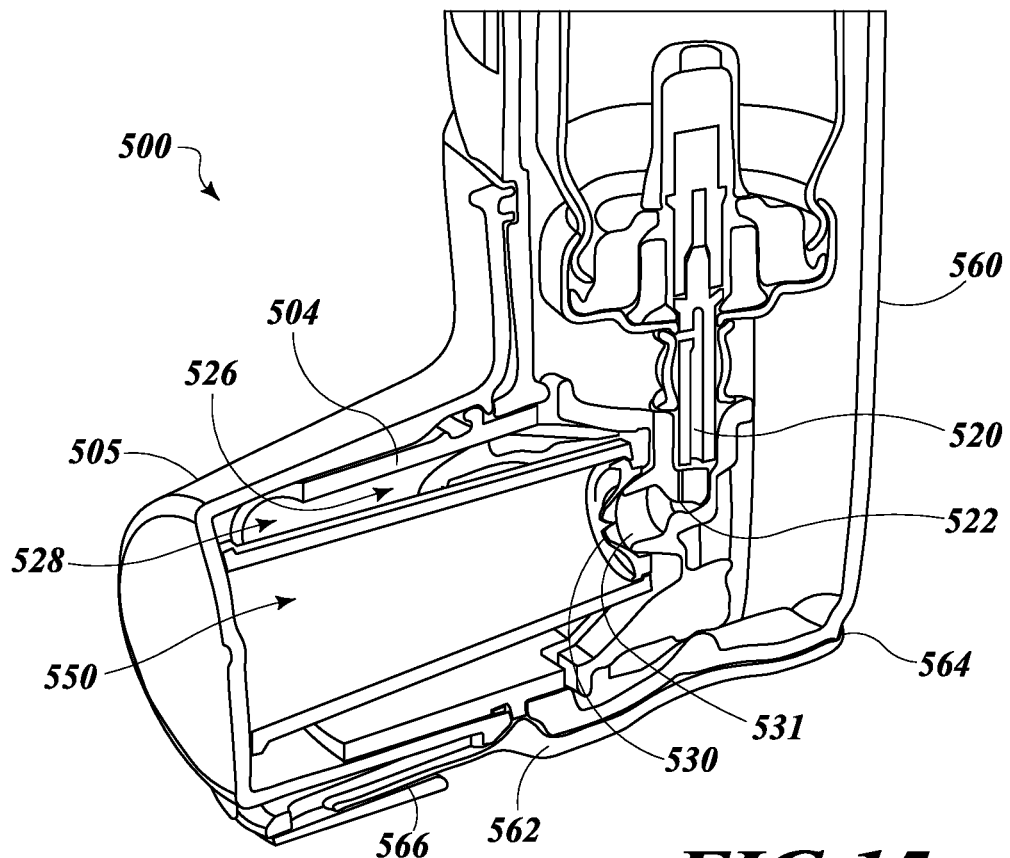
FIG. 15 is an isometric cross-sectional view of a portion of an aerosol delivery unit, according to another embodiment, which includes a mouthpiece cap having a desiccant chamber therein and a seal member for selectively isolating a discharge passageway of the aerosol delivery unit from the external environment.

In still yet other embodiments, desiccant material may be provided within other components of the host aerosol delivery unit, including, for example, within a mouthpiece cap used to cover the mouthpiece aperture of the aerosol delivery unit when not in use. For example, FIG. 15 shows one example embodiment of an aerosol delivery unit 500, which includes a mouthpiece cap 505 for covering a mouthpiece 504 of the aerosol delivery unit 500 having a mouthpiece aperture 528 that is in fluid communication with an inhalation passageway 526 through which aerosolized matter is discharged during operation of the aerosol delivery unit 500. A desiccant chamber 550 containing a desiccant material (not shown) is provided within the mouthpiece cap 505, and the mouthpiece cap 505 includes a seal member 530 (shown in a non-deformed state), such as a split seal valve, an umbrella valve or other seal valve, which is configured to close upon removal of the mouthpiece cap 505 from a mouthpiece 504 of the aerosol delivery unit 500 in order to isolate the desiccant material in the desiccant chamber 550 from the external environment when the mouthpiece cap 505 is removed. The seal member 530 is arranged within the mouthpiece cap 505 and a protrusion 531 is provided within the inhalation passageway 526 to displace the seal member 530 to bring the desiccant chamber 550 into fluid communication with a discharge orifice 522 and a discharge passageway 520 of the unit 500 located upstream of the inhalation passageway 526 when the mouthpiece cap 505 is installed over the mouthpiece 504 to prevent access to the inhalation passageway 526. In this manner, when the mouthpiece cap 505 is secured over the mouthpiece 504, the discharge orifice 522 and discharge passageway 520 are isolated from the inhalation passageway 526 and the external environment while also being exposed to desiccant within the desiccant chamber 550. Conversely, when the mouthpiece cap 505 is removed, the discharge passageway 520 and discharge orifice 522 are brought into fluid communication with the inhalation passageway 526.

In order to prevent loss of the mouthpiece cap 505 and help ensure that it will be replaced on the mouthpiece 504 after a user receives a dose or doses of the aerosolized matter, the mouthpiece cap 505 may be tethered to a housing 560 of the aerosol delivery unit 500 by a tether member 562 connected to the housing 560 via a living hinge 564 or other connection. In addition, the mouthpiece cap 505 may be connected to the tether member 562 by a sliding joint 566 that enables the mouthpiece cap 505 to be withdrawn from the mouthpiece 504 before the mouthpiece cap 505 is rotated away from the end of the unit 500 containing the mouthpiece aperture 528.

Figure 16:
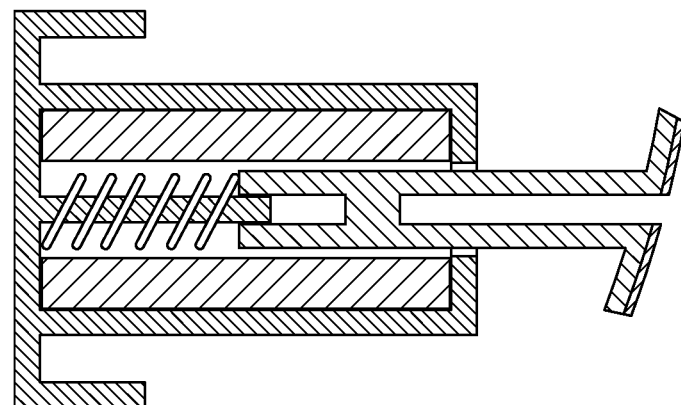
FIG. 16 is a schematic diagram of an alternate arrangement of a mouthpiece cap having a desiccant chamber therein and a seal member for selectively isolating a discharge passageway of the aerosol delivery unit from the external environment.

Although the seal member 530 shown in the example embodiment of FIG. 15 is shown as a deformable membrane (e.g., split seal valve), it is appreciated that a variety of other types of seal arrangements may be used in lieu thereof (e.g., umbrella valve or other valve that is configured to close upon removing the mouthpiece cap and to open when the mouthpiece cap is installed). For example, with reference to FIG. 16, a mouthpiece cap may be provided with a seal member comprising a spring-biased plunger element that is actuated in a direction opposite a bias applied by a spring thereof when the mouthpiece cap closes the mouthpiece aperture to thereby expose the discharge passageway to the desiccant material.

It is further appreciated that embodiments disclosed herein may be provided in the form of a manually actuatable inhaler (also referred to as a press-and-breathe inhaler) or a breath actuated inhaler, including mechanical power actuated inhalers and electrical power (i.e., electromechanical) actuated inhalers. Accordingly, in some embodiments, the aerosol delivery units described herein may further include, among other things, a power source (mechanical or electrical) and an actuator coupled to the power source for moving the canister from the initial position to the discharge position to deliver the dose of aerosolized matter, such as in response to a user inhaling on the aerosol delivery unit or other trigger event. Moreover, in some embodiments, movement of the seal members disclosed herein may be electronically controlled and coordinated with movement of the canister. Still further, it is appreciated that aspects and features of the embodiments disclosed herein may be incorporated in or adapted for use with a dry powder inhaler (DPI) apparatus or a variety of other drug delivery apparatuses having a drug delivery tract.

It will also be appreciated that in view of the present disclosure related methods of making and operating a drug delivery apparatus may be provided. For example, one example embodiment of a method of controlling the environment within a drug delivery tract of a drug delivery apparatus may be summarized as including: discharging a dose of a drug through the drug delivery tract; isolating at least a portion of the drug delivery tract to form an isolated environment within the drug delivery apparatus; and desiccating the isolated environment to reduce water vapor content therein. The method may further include unsealing the at least a portion of the drug delivery tract; and discharging a subsequent dose of the drug through the drug delivery tract, wherein unsealing the at least a portion of the drug delivery tract is coordinated with actuation of the aerosol canister such that the delivery tract is completely unobstructed as the drug formulation passes through the drug delivery tract. Discharging the dose of the drug may include discharging a moisture sensitive formulation through the drug delivery tract, and desiccating the isolated environment may substantially prevent the accumulation of drug residue within the at least a portion of the drug delivery tract throughout operation of the drug delivery apparatus. In some instances, discharging the dose of the drug may include discharging the drug formulation through a discharge valve of an aerosol canister into the drug delivery tract, and isolating the at least a portion of the drug delivery tract may include sealing the at least a portion of the drug delivery tract at or downstream of a discharge orifice through which the drug formulation is dispersed after being discharged through the discharge valve of the aerosol canister.

As another example, an embodiment of operating a drug delivery apparatus in the form of an aerosol delivery unit may be summarized as including: discharging at least one dose of aerosolized matter through an inhalation passageway that is in fluid communication with a discharge passageway extending from an outlet of an aerosol canister discharge valve toward the inhalation passageway, and thereafter, sealing the discharge passageway to isolate the discharge passageway from the inhalation passageway and an environment external to the aerosol delivery unit. The method may further include temporarily storing the aerosol delivery unit with the discharge passageway isolated from the inhalation passageway, and, prior to discharging at least one other dose of aerosolized matter through the inhalation passageway, unsealing the discharge passageway such that the discharge passageway and the inhalation passageway are in fluid communication. The method may further include exposing the discharge passageway to a desiccant material at least while temporarily storing the aerosol delivery unit.

Although embodiments are shown and described herein largely in the context of aerosol delivery units that are well adapted to both temporarily seal the discharge passageway and to expose the discharge passageway to a desiccant material, it is appreciated that some embodiments may include only some of this functionality, namely, exposing the discharge passageway to a desiccant material without sealing the passageway off from the adjacent and downstream inhalation passageway, or selectively sealing off the discharge passageway without exposing the sealed passageway to a desiccant material. Regarding the former, the desiccant material may be positioned to be in fluid communication with the discharge passageway through the aperture in the side of the valve stem of the canister, through the discharge orifice, through a passageway in a valve stem block, or a combination thereof, without providing a seal arrangement to seal off the discharge passageway.

For example, the desiccant arrangement shown in FIGS. 3A and 3B may be employed without the displaceable seal member 130. For instance, FIGS. 19 through 21B show another example embodiment of an aerosol delivery unit 700 for selectively delivering a dose of aerosolized matter (referred to generally as a metered dose inhaler or MDI), which includes structures and associated functionality for exposing the discharge passageway to a desiccant material without having a seal member for sealing the discharge passageway off from the adjacent and downstream inhalation passageway.

Figure 21A:
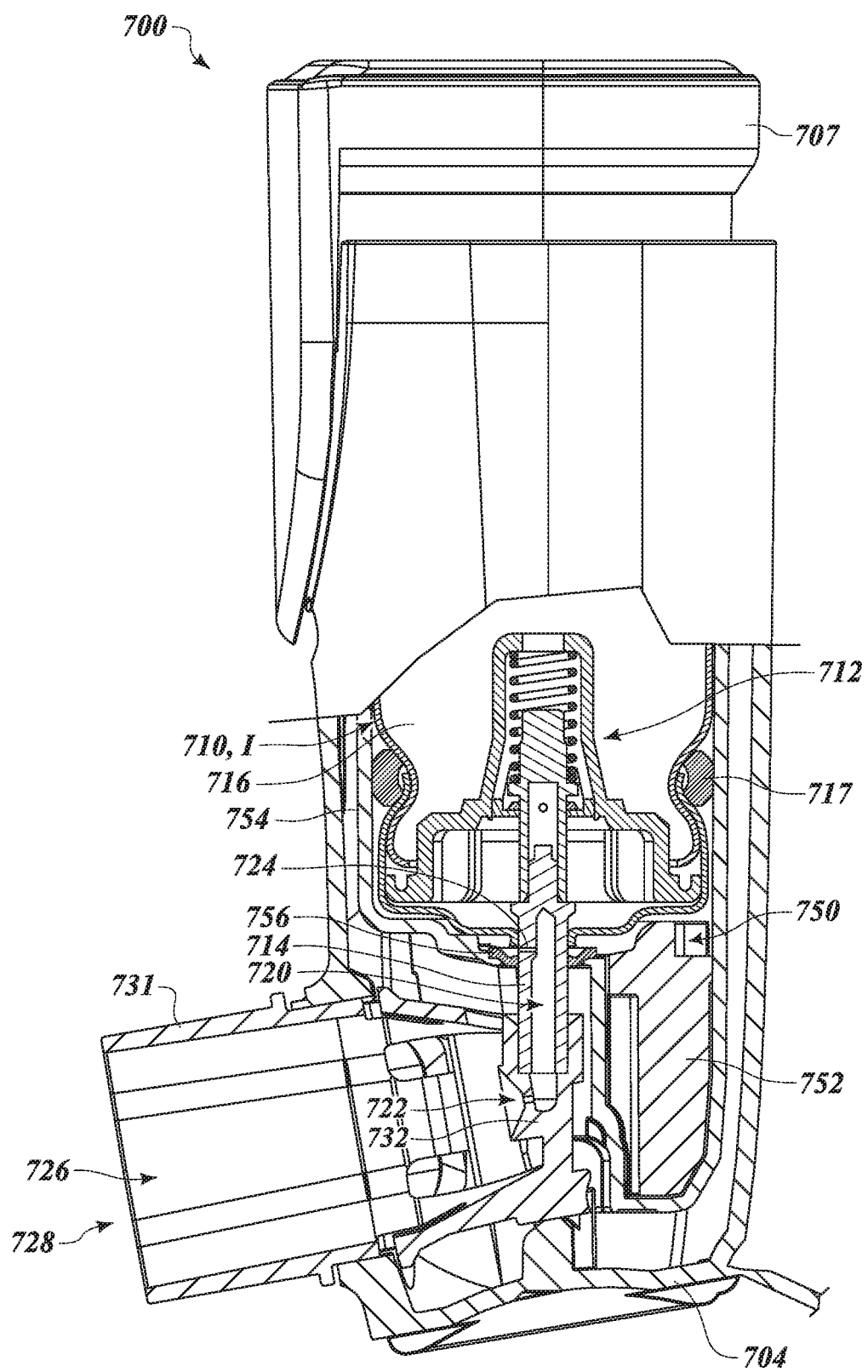
FIG. 21A is a side view of the aerosol delivery unit of FIG. 19 with a portion thereof illustrated in cross-section, showing the unit in a standby or storage configuration in which the discharge passageway is exposed to a desiccant material.
Figure 21B:
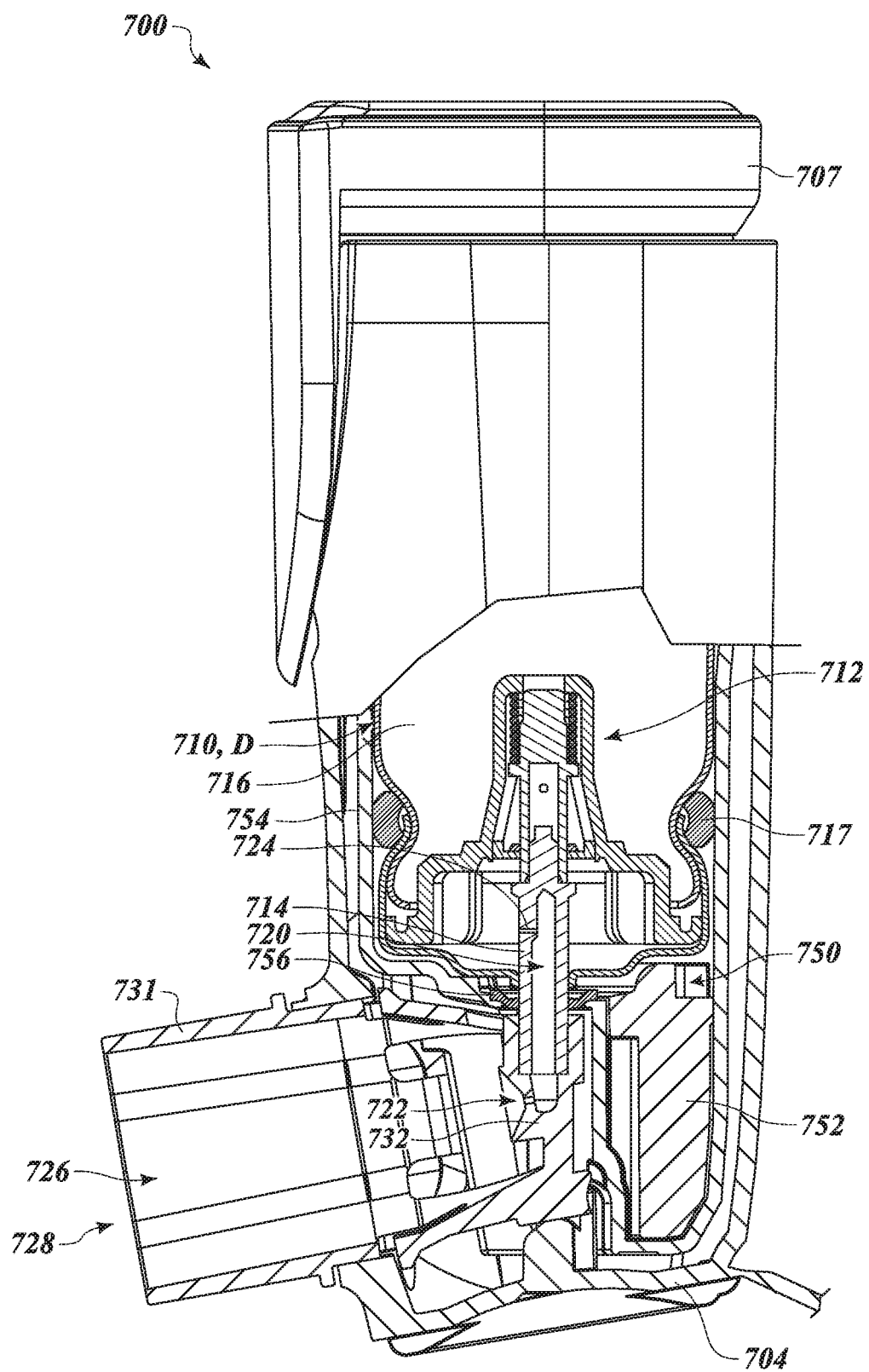
FIG. 21B is a side view of the aerosol delivery unit of FIG. 19 with a portion thereof illustrated in cross-section, showing the unit in a discharge configuration in which the discharge passageway is temporarily isolated from the desiccant material as aerosolized matter is discharged from the canister into an inhalation passageway for delivery to a user.

With reference to FIGS. 19 through 21B, the aerosol delivery unit 700 includes a base housing 704 and a canister 710 received in the base housing 704, the canister 710 being displaceable from an initial position I, as shown in FIG. 21A, to a discharge position D, as shown in FIG. 21B, for selectively discharging a dose of aerosolized matter for inhalation by a user. The canister 710 comprises a canister body 716, which contains the matter to be discharged, and an outlet valve member 712, which includes a movable valve stem 714 that extends from the canister body 716. The valve stem 714 defines a portion of a discharge passageway 720 extending from the canister body 716 to a discharge orifice 722 provided within the aerosol delivery unit 700, which in turn leads to an inhalation passageway 726 through which the aerosolized matter passes before being discharged through a mouthpiece aperture 728 for inhalation by the user during an inhalation event. The discharge passageway 720 and the inhalation passageway 726 may be collectively referred to as a drug delivery tract. As will be appreciated by those of ordinary skill in the relevant art, when the valve stem 714 is displaced relative to the canister body 716, as shown in FIG. 21B, a metered dose of the matter contained with the canister body 716 will be discharged through the discharge orifice 722 for inhalation by a user via the inhalation passageway 726.

With reference to FIG. 19, the aerosol delivery unit 700 may further include a dose counter assembly 707 secured to an upper under of the canister 710 to provide dose counting functionality and to provide a user interface for depressing the canister 710. The aerosol delivery unit 700 may also include a cap 705 to cover the mouthpiece aperture 728 of the aerosol delivery unit 700 when storing the unit 700. The cap 705 may be completely separable from the base housing 704, or may be coupled to the base housing 704 by a tether 706, which enables the cover 705 to be removed from the mouthpiece aperture 728 while still remaining coupled to the base housing 704.

With reference to FIGS. 21A and 21B, the aerosol delivery unit 700 further includes a desiccant chamber 750 containing a desiccant material 752 that is in fluid communication with the discharge passageway 720 at least when the aerosol delivery unit 700 is in a storage configuration and not actively discharging aerosolized matter. For example, in accordance with the example embodiment shown in FIGS. 21A and 21B, the desiccant chamber 750 is provided at an end of the canister 710 between a lower end of the canister body 716 and a separate desiccant housing 754 and stem seal 756 that are coupled to the end of the canister 710. The desiccant material 752 may be provided in a semi-annular form (as shown in FIG. 20) and may include a central passage 753 through which the valve stem 714 of the canister 710 extends. The stem seal 756 may be an annular seal formed integrally with the desiccant housing 754, such as, for example, via a multi-shot injection molding process, or may otherwise be provided as a separate seal component coupled to the desiccant housing 754. In some instances, the stem seal 756 may be provided as a bellows type seal that is secured between the valve stem 714 and the desiccant housing 754 to provide a desiccant chamber 750 having a volume that varies as the stem seal 756 is deformed as the canister 710 is displaced during an inhalation event. In other instances, such as the example embodiment shown in FIGS. 21A and 21B, the desiccant chamber 750 may have a fixed volume.

As can be appreciated from FIG. 21A, the desiccant material 752 within the desiccant chamber 750 is in fluid communication with the discharge passageway 720 through an aperture 724 in the side of the valve stem 714 that is otherwise used to pass the matter contained in the canister body 716 toward the discharge orifice 722 when the valve stem 714 is displaced during an inhalation event. In this manner, the discharge passageway 720 remains exposed to the desiccant material 752 when the canister 710 is in the initial position I, such as when storing the unit 700. In some instances, the desiccant material may be sufficient to keep the discharge passageway dry (e.g., <25% RH) between uses for substantially the entire product life of the canister of material to be discharged.

Advantageously, the desiccant housing 754 may be coupled to the end or collar of the canister 710 to form a cartridge 760 (FIG. 20) that is readily removable from the base housing 704. In this manner, the desiccant housing 754 and canister 710 may be easily removed from the base housing 704 to replace the canister 710 when depleted and/or to replace the desiccant material 752 as desired. The desiccant housing 754 may be coupled to the end or collar of the canister 710 via a resilient band, clips, detents or other fastening devices or techniques, including friction fit or interference fit arrangements. Although the desiccant chamber 750 is shown in the example embodiment of FIGS. 21A and 21B as being coupled to a lower end or collar of the canister 710, it is appreciated that in other embodiments a desiccant chamber may be provided in a separate desiccant housing that is coupled to the base housing 704 separate from the canister 710, the desiccant chamber may be formed integrally in the base housing itself, or the desiccant chamber may be provided in a separate component that is attached to the base housing 704. In addition, the desiccant material may be provided in a variety of different forms, such as gel form, powder form, granular form or molded form, and may consist of or comprise different materials, such as silica, activated charcoal, calcium sulfate or calcium chloride.

According to the example embodiment of FIGS. 19 through 21B, the desiccant housing 754 may be coupled to the end or collar of the canister 710 to form a cartridge 760 that is installable in the base housing 704 to engage a stem block 732 provided therein. Further details of the components of the cartridge 160 and the stem block 732 can be seen in the exploded view of FIG. 20. As shown in FIG. 20, the desiccant housing 754 may form a cup-like structure with a generally cylindrical sidewall that is sized and shaped to receive a lower end of the canister 710. The desiccant material 752 may be provided in a molded form. The desiccant material 752 may be configured to be positioned in a lower end of the desiccant housing 754. The desiccant housing 754 may include one or more locating or coupling features to assist in joining or otherwise positioning the desiccant material 752 within the desiccant housing 754. The desiccant material 752 may be shaped so as to not obstruct a valve stem aperture of the stem seal 756 provided in the desiccant housing 754 for receiving the valve stem 714 of the canister 710. For example, the desiccant material 752 may have a semi-annular shape with a central passage 753 or other clearance for the valve stem 714. In some instances, such as in the example embodiment shown in FIGS. 19 through 21B, the desiccant material 752 may be shaped to partially encircle the valve stem 714 and may extend beyond a terminal end of the valve stem 714. The desiccant housing 754 and the desiccant material 752 may also be correspondingly shaped, and may each extend beyond a terminal end of the valve stem 714. In this manner, the desiccant material 752 may substantially fill the desiccant chamber 750 and provide a relatively large volume of desiccant material suitable to continuously remove moisture at least from the passage of the valve stem 714 throughout the usable life of the material (e.g., drug formulation) contained in the canister 710.

With reference to FIGS. 21A and 21B, a canister seal 717 may be positioned around the canister body 716, such as around a lower neck portion thereof, to provide a resilient member between the canister body 716 and the desiccant housing 754 which may be compressed when the canister 710 and the desiccant housing 754 are coupled together. The canister seal 717 may provide a seal location to assist in isolating the desiccant chamber 750 when the aerosol delivery unit 700 is fully assembled and in preventing the ingress of moisture into said desiccant chamber 750 other than through the discharge passageway 720. In a similar manner, the stem seal 756 may provide a seal location to assist in isolating the desiccant chamber 750 when the aerosol delivery unit 700 is fully assembled and in preventing the ingress of moisture into said desiccant chamber 750. In this manner, the desiccant chamber 750 is effectively isolated from the external environment apart from the discharge passageway 720, which may be exposed to the external environment through the inhalation passageway 726 when the mouthpiece cap 705 is removed from the base housing 704.

As can be appreciated from a review of FIGS. 21A and 21B, when the valve stem 714 is in an expanded position, the portion of the discharge passageway 720 defined by the valve stem 714 is in fluid communication with the desiccant chamber 752 via the aperture 724 in the side of the valve stem 714. Conversely, when the valve stem 714 of the canister 710 is fully depressed, the desiccant chamber 752 is temporarily isolated from the discharge passageway 720 defined by the valve stem 714.

Again, with the canister 700 loaded in the desiccant housing 754, the valve stem 714 protrudes from a lower end thereof to be subsequently received in the nozzle block 732 provided in the base housing 704. According to the example embodiment of FIG. 20, the nozzle block 732 may be provided in a mouthpiece unit 731 that is coupleable to the base housing 704 and includes the inhalation passageway 726 and the mouthpiece aperture 728 for delivering aerosolized matter to the user. As illustrated, when the cartridge 760 is installed, the desiccant material 752 may extend from a location above the discharge orifice 722 of the nozzle block 732 to a location below the discharge orifice 722, and may substantially fill the desiccant chamber 750 within the desiccant housing 754 to provide a relatively large volume of desiccant material suitable to continuously remove moisture at least from the passage of the valve stem 714 throughout the usable life of the material (e.g., drug formulation) contained in the canister 710. In this manner, embodiments may be particularly well suited to eliminate, reduce or minimize the presence of moisture in the discharge passageway 720 and to eliminate, reduce or minimize any fouling associated therewith even when not completely isolating the discharge passageway 720 from the external environment after discharging the material during the inhalation event.

Moreover, aspects and features of the various embodiments described above may be combined to provide yet further embodiments. U.S. Provisional Patent Application No. 62/569,901, filed Oct. 9, 2017 and U.S. Provisional Patent Application No. 62/639,911, filed Mar. 7, 2018, to which the present application claims priority, are hereby incorporated herein by reference in their entirety. Aspects of the embodiments can be modified, if necessary to employ concepts of the applications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:
1. A drug delivery device comprising:
   a canister containing a drug formulation and having a discharge valve and a valve stem defining a valve stem passage through which the drug formulation is selectively discharged;
   a base housing including an inhalation passageway through which the drug formulation is discharged during an inhalation event;
   a valve stem block including a discharge orifice in fluid communication with the inhalation passageway from which the drug formulation is ejected during the inhalation event after passing through the valve stem passage;
   a desiccant housing attached to the canister with the valve stem extending through the desiccant housing;
   a desiccant material provided in the desiccant housing in fluid communication with the valve stem passage;
   wherein the canister, the desiccant housing and the desiccant material form a cartridge that is removably installable in the base housing with the valve stem of the canister engaging the valve stem block when the cartridge is installed; and wherein, when the cartridge is installed, the desiccant material extends from a location above the discharge orifice of the valve stem block to a location below the discharge orifice.

2. The drug delivery device of claim 1 wherein the valve stem of the canister includes an aperture in a side thereof, and wherein, when the valve stem is in an expanded position, the valve stem passage is in fluid communication with the desiccant material via the aperture in the side of the valve stem.

3. The drug delivery device of claim 1 wherein the canister is removably installable in the desiccant housing and a canister seal is positioned between the desiccant housing and the canister to assist in at least partially isolating the desiccant material from an external environment of the drug delivery device.

4. The drug delivery device of claim 1 wherein the desiccant housing includes a stem seal formed integrally therewith through which the valve stem extends, the stem seal assisting in at least partially isolating the desiccant material from an external environment of the drug delivery device.

5. The drug delivery device of claim 1 wherein the desiccant material is an annular or semi-annular molded component.

6. The drug delivery device of claim 1 wherein the desiccant material is a semi-annular molded component, which partially encircles the valve stem and extends beyond a terminal end of the valve stem.

7. The drug delivery device of claim 1 wherein the desiccant housing and the desiccant material are correspondingly shaped, and wherein each of the desiccant housing and the desiccant material extend beyond a terminal end of the valve stem.

8. The drug delivery device of claim 1 wherein, apart from when the valve stem is depressed, the desiccant material is arranged to continuously remove moisture at least from the valve stem passage defined by the valve stem throughout the usable life of the drug formulation contained in the canister.

9. The drug delivery device of claim 1 wherein, when the valve stem of the canister is fully depressed, the desiccant material is isolated from the valve stem passage and an external environment of the drug delivery device.

10. The drug delivery device of claim 1, further comprising:
- a mouthpiece aperture in fluid communication with the inhalation passageway through which the drug formulation is discharged during the inhalation event; and
- a desiccant chamber within the desiccant housing in which the desiccant material is contained, the desiccant chamber being in fluid communication with the valve stem passage at least when the drug delivery device is in a storage configuration.

11. The drug delivery device of claim 10, wherein the desiccant housing and the canister collectively define the desiccant chamber within which the desiccant material is contained.

12. The drug delivery device of claim 1, wherein the drug delivery device is a metered dose inhaler.

13. The drug delivery device of claim 12, wherein the drug formulation comprises a medicament suitable for use in bronchodilation therapy.

14. The drug delivery device of claim 10, wherein the drug delivery device is a metered dose inhaler.

15. The drug delivery device of claim 14, wherein the drug formulation comprises a medicament suitable for bronchodilation therapy.

* * * * *